(12) United States Patent
Tung et al.

(10) Patent No.: US 6,608,067 B1
(45) Date of Patent: Aug. 19, 2003

(54) INHIBITORS OF SERINE PROTEASES, PARTICULARLY HCV NS3 PROTEASE

(75) Inventors: Roger D. Tung, Beverly, MA (US); Govinda Rao Bhisetti, Lexington, MA (US); Luc J. Farmer, Foxoboro, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 09/677,382

(22) Filed: Sep. 29, 2000

Related U.S. Application Data

(63) Continuation of application No. PCT/US99/07149, filed on Mar. 31, 1999.
(60) Provisional application No. 60/080,060, filed on Mar. 31, 1998.

(51) Int. Cl.$^7$ ........................ A61K 31/495; A61K 31/16; A61K 31/44; A61K 31/675; A61P 31/18
(52) U.S. Cl. ..................... 514/255.06; 514/85; 514/616; 544/337; 544/406; 546/298; 564/153
(58) Field of Search .............................. 514/85, 255.06, 514/350, 616; 544/337, 406; 546/298; 564/153

(56) References Cited

FOREIGN PATENT DOCUMENTS

| DE | 19648793 | 5/1998 |
|---|---|---|
| WO | WO96/33209 | 10/1996 |

*Primary Examiner*—Brenda Coleman
(74) *Attorney, Agent, or Firm*—Lisa A. Dixon; Vertex Pharmaceuticals Incorporated

(57) ABSTRACT

The present invention relates to compounds, methods and pharmaceutical compositions for inhibiting proteases, particularly serine proteases, and more particularly HCV NS3 proteases. The compounds, and the compositions and methods that utilize them, can be used, either alone or in combination to inhibit viruses, particularly HCV virus.

13 Claims, No Drawings

INHIBITORS OF SERINE PROTEASES, PARTICULARLY HCV NS3 PROTEASE

CROSS-REFERENCE TO RELATED APPLICATIONS

This application is a continuing application of co-pending International Patent Application PCT/US99/07149, filed Mar. 31, 1999, which was published Oct. 7, 1999 under PCT Article 21 (2) in English as Publication No. WO 99/50230, which claims the benefit of United States provisional patent application No. 60/080,060, filed Mar. 31, 1998.

TECHNICAL FIELD OF THE INVENTION

The present invention relates to compounds that are useful as protease inhibitors, particularly as serine protease inhibitors, and more particularly as hepatitis C NS3 protease inhibitors. As such, they act by interfering with the life cycle of the hepatitis C virus and are also useful as antiviral agents.

This invention also relates to pharmaceutical compositions comprising these compounds. The compounds and pharmaceutical compositions of this invention are particularly well suited for inhibiting HCV NS3 protease activity and consequently, may be advantageously used as therapeutic agents against the hepatitis C virus and other viruses that are dependent upon a serine protease for proliferation. This invention also relates to methods for inhibiting the activity of proteases, including hepatitis C virus NS3 protease and other serine proteases, using the compounds of this invention and related compounds.

BACKGROUND OF THE INVENTION

Infection by hepatitis C virus ("HCV") is a compelling human medical problem. HCV is recognized as the causative agent for most cases of non-A, non-B hepatitis, with an estimated human seroprevalence of 1% globally [Purcell, R. H., "Hepatitis C virus: Historical perspective and current concepts" *FEMS Microbiology Reviews* 14, pp. 181–192 (1994); Van der Poel, C. L., "Hepatitis C Virus. Epidemiology, Transmission and Prevention in Hepatitis C Virus. Current Studies in Hematology and Blood Transfusion, H. W. Reesink, Ed., (Basel: Karger), pp. 137–163 (1994)]. Four million individuals may be infected in the United States alone [Alter, M. J. and Mast, E. E., "The Epidemiology of Viral Hepatitis in the United States, *Gastroenterol. Clin. North Am.* 23, pp. 437–455 (1994)].

Upon first exposure to HCV only about 20% of infected individuals develop acute clinical hepatitis while others appear to resolve the infection spontaneously. In most instances, however, the virus establishes a chronic infection that persists for decades [Iwarson, S. "The Natural Course of Chronic Hepatitis" *FEMS Microbiology Reviews* 14, pp. 201–204 (1994)]. This usually results in recurrent and progressively worsening liver inflammation, which often leads to more severe disease states such as cirrhosis and hepatocellular carcinoma [Kew, M. C., "Hepatitis C and Hepatocellular Carcinoma", *FEMS Microbiology Reviews*, 14, pp. 211–220 (1994); Saito, I., et al. "Hepatitis C Virus Infection is Associated with the Development of Hepatocellular Carcinoma" *Proc. Natl. Acad. Sci. USA* 87, pp. 6547–6549 (1990)]. Unfortunately, there are no broadly effective treatments for the debilitating progression of chronic HCV.

The HCV genome encodes a polyprotein of 3010–3033 amino acids [Choo, Q. -L., et al. "Genetic organization and Diversity of the Hepatitis C Virus", *Proc. Natl. Acad. Sci. USA*, 88, pp. 2451–2455 (1991); Kato, N. et al., Molecular Cloning of the Human Hepatitis C Virus Genome From Japanese Patients with Non-A, Non-B Hepatitis", *Proc. Natl. Acad. Sci. USA*, 87, pp. 9524–9528 (1990); Takamizawa, A. et al., "Structure and organization of the Hepatitis C Virus Genome Isolated From Human Carriers", *J. Virol.*, 65, pp. 1105–1113 (1991)]. The HCV nonstructural (NS) proteins are presumed to provide the essential catalytic machinery for viral replication. The NS proteins are derived by proteolytic cleavage of the polyprotein [Bartenschlager, R. et al., "Nonstructural Protein 3 of the Hepatitis C Virus Encodes a Serine-Type Proteinase Required for Cleavage at the NS3/4 and NS4/5 Junctions", *J. Virol.*, 67, pp. 3835–3844 (1993); Grakoui, A. et al. "Characterization of the Hepatitis C Virus-Encoded Serine Proteinase: Determination of Proteinase-Dependent Polyprotein Cleavage Sites", *J. Virol.*, 67, pp. 2832–2843 (1993); Grakoui, A. et al., Expression and Identification of Hepatitis C Virus Polyprotein Cleavage Products", *J. Virol.*, 67, pp. 1385–1395 (1993); Tomei, L. et al., "NS3 is a serine protease required for processing of hepatitis C virus polyprotein", *J. Virol.*, 67, pp. 4017–4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898–8902 (1990)]. The first 181 amino acids of NS3 (residues 1027–1207 of the viral polyprotein) have been shown to contain the serine protease domain of NS3 that processes all four downstream sites of the HCV polyprotein [C. Lin et al., "Hepatitis C Virus NS3 Serine Proteinase: Trans-Cleavage Requirements and Processing Kinetics", *J. Virol.*, 68, pp. 8147–8157 (1994)].

The HCV NS3 serine protease and its associated cofactor, NS4A, helps process all of the viral enzymes, and is thus considered essential for viral replication. This processing appears to be analogous to that carried out by the human immunodeficiency virus aspartyl protease, which is also involved in viral enzyme processing HIV protease inhibitors, which inhibit viral protein processing are potent antiviral agents in man, indicating that interrupting this stage of the viral life cycle results in therapeutically active agents. Consequently it is an attractive target for drug discovery. Unfortunately, there are no serine protease inhibitors available currently as anti-HCV agents.

Furthermore, the current understanding of HCV has not led to any other satisfactory anti-HCV agents or treatments. The only established therapy for HCV disease is interferon treatment. However, interferons have significant side effects (Janssen et al., 1994; Renault and Hoofnagle, 1989) [Janssen, H. L. A., et al. "Suicide Associated with Alfa-Interferon Therapy for Chronic Viral Hepatitis" *J. Hepatol.*, 21, pp. 241–243 (1994)]; Renault, P. F. and Hoofnagle, J. H., "Side effects of alpha interferon. Seminars in Liver Disease 9, 273–277. (1989)] and induce long term remission in only a fraction (~25%) of cases [Weiland, O. "Interferon Therapy in Chronic Hepatitis C Virus Infection", *FEMS Microbiol. Rev.*, 14, PP. 279–288 (1994)]. Moreover, the prospects for effective anti-HCV vaccines remain uncertain.

Thus, there is a need for more effective anti-HCV therapies. Such inhibitors would have therapeutic potential as protease inhibitors, particularly as serine protease inhibitors, and more particularly as HCV NS3 protease inhibitors. Specifically, such compounds may be useful as antiviral agents, particularly as anti-HCV agents.

SUMMARY OF THE INVENTION

The present invention provides compounds, and pharmaceutically acceptable derivatives thereof, that are useful as protease inhibitors, particularly as serine protease inhibitors, and more particularly as HCV NS3 protease inhibitors. These compounds can be used alone or in combination with immunomodulatory agents, such as α-, β- or γ-interferons; other antiviral agents such as ribavirin and amantadine; other inhibitors of hepatitis C protease; inhibitors of other targets in the HCV life cycle including the helicase, polymerase, metalloprotease, or internal ribosome entry; or combinations thereof.

The present invention also provides methods for inhibiting proteases, particularly serine proteases, and more particularly HCV NS3 protease.

The present invention also provides pharmaceutical compositions comprising the compounds of this invention, as well as multi-component compositions comprising additional immunomodulatory agents, such as α-, β- or γ-interferons; other antiviral agents such as ribavirin and amantadine; other inhibitors of hepatitis C protease; inhibitors of other targets in the HCV life cycle including the helicase, polymerase, metalloprotease, or internal ribosome entry; or combinations thereof. The invention also provides methods of using the compounds of this invention, as well as other related compounds, for the inhibition of HCV.

DETAILED DESCRIPTION OF THE INVENTION

In order that the invention herein described may be more fully understood, the following detailed description is set forth. In the description, the following abbreviations are used:

| Designation | Reagent or Fragment |
|---|---|
| Abu | aminobutyric acid |
| Ac | acetyl |
| AcOH | acetic acid |
| Bn | benzyl |
| Boc | tert-butyloxycarbonyl |
| Bz | benzoyl |
| Cbz | carbobenzyloxy |
| CDI | carbonyldiimidazole |
| DCE | 1,2-dichloroethane |
| DCM | dichloromethane |
| DIEA | diisopropylethylamine |
| DMA | dimethylacetamide |
| DMAP | dimethylaminopyridine |
| DMF | dimethylformamide |
| DPPA | diphenylphosphorylazide |
| DMSO | dimethylsulfoxide |
| Et | ethyl |
| EtOAc | ethyl acetate |
| FMOC | 9-fluorenylmethoxycarbonyl |
| HbtU | O-benzotriazolyl-N,N,N',N'-tetramethyluronium hexafluorophosphate |
| HOBt | N-hydroxybenzotriazole |
| HPLC | high performance liquid chromatography |
| Me | methyl |
| MS | mass spectrometry |
| NMP | N-methyl pyrrolidinone |
| ND | not determined |
| Pip | piperidine |

-continued

| Designation | Reagent or Fragment |
|---|---|
| Prz | piperazine |
| PyBrop | bromo-tris-pyrrolidinophosphonium hexafluorophosphate |
| Pyr | pyridine |
| THF | tetrahydrofuran |
| TFA | trifluoroacetic acid |
| TFE | trifluoroethanol |
| Tol | toluene |

The following terms are used herein:

Unless expressly stated to the contrary, the terms "—$SO_2$—" and "—$S(O)_2$—" as used herein refer to a sulfone or sulfone derivative (i.e., both appended groups linked to the S), and not a sulfinate ester.

The term "substituted" refers to the replacement of one or more hydrogen radicals in a given structure with a radical selected from a specified group. When more than one hydrogen radical may be replaced with a substituent selected from the same specified group, the substituents may be either the same or different at every position.

As used herein, the term "amino" refers to a trivalent nitrogen which may be primary or which may be substituted with 1–2 alkyl groups.

The term "alkyl" or "alkane", alone or in combination with any other term, refers to a straight-chain or branched-chain saturated aliphatic hydrocarbon radical containing the specified number of carbon atoms, or where no number is specified, preferably from 1–10 and more preferably from 1–5 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl" or "alkene", alone or in combination with any other term, refers to a straight-chain or branched-chain mono- or poly-unsaturated aliphatic hydrocarbon radical containing the specified number of carbon atoms, or where no number is specified, preferably from 2–10 carbon atoms and more preferably, from 2–5 carbon atoms. Examples of alkenyl radicals include, but are not limited to, ethenyl, E- and Z-propenyl, E- and Z-isobutenyl, E- and Z-pentenyl, E- and Z-hexenyl, E,E-, E,Z-, Z,E-, and Z-Z-hexadienyl and the like.

The term "alkynyl" or "alkyne", alone or in combination with any other term, refers to a straight-chain or branched-chain mono or poly-unsaturated aliphatic hydrocarbon radical containing the specified number of carbon atoms, or where no number is specified, preferably from 2–10 carbon atoms and more preferably, from 2–5 carbon atoms, wherein at least one of the unsaturated aliphatic hydrocarbon radicals comprises a triple bond. Examples of alkynyl radicals include, but are not limited to, ethynyl, propynyl, isobutynyl, pentynyl, hexynyl, hexenynyl, and the like.

The term "aryl", alone or in combination with any other term, refers to a carbocyclic aromatic radical containing the specified number of carbon atoms, and which may be optionally fused, for example benzofused, with one to three cycloalkyl, aromatic, heterocyclic or heteroaromatic rings. Preferred aryl groups have from 6–14 carbon atoms, and more preferred groups from 6–10 carbon atoms. Examples of aryl radicals include, but are not limited to, phenyl, naphthyl, anthracenyl and the like.

The term "carbocycle", alone or in combination with any other term, refers to a stable non-aromatic 3- to 8-membered carbon ring radical which may be saturated, Amono-unsaturated or poly-unsaturated, and which may be optionally fused, for example benzofused, with one to three cycloalkyl, aromatic, heterocyclic or heteroaromatic rings. The carbocycle may be attached at any endocyclic carbon atom which results in a stable structure.

The terms "cycloalkyl" or "cycloalkane", alone or in combination with any other term, refers to a stable non-aromatic 3- to 8-membered carbon ring radical which is saturated and which may be optionally fused, for example benzofused, with one to three cycloalkyl, aromatic, heterocyclic or heteroaromatic rings. The cycloalkyl may be attached at any endocyclic carbon atom which results in a stable structure. Preferred carbocycles have 5 to 6 carbons. Examples of carbocycle radicals include, but are not limited to, cyclopropyl, cyclbutyl, cyclpentyl, cyclohexyl, cycloheptyl, cyclopentenyl, cyclohexenyl, indane, tetrahydronaphthalene and the like.

The term "cycloalkenyl" or "cycloalkene" alone or in combination with any other term, refers to a stable cyclic hydrocarbon ring radical containing at least one endocyclic carbon-carbon double bond. The carbocycle may be attached at any cyclic carbon atom which results in a stable structure. Where no number of carbon atoms is specified, a cycloalkenyl radical preferably has from 5–7 carbon atoms. Examples of cycloalkenyl radicals include, but are not limited to, cyclopentenyl, cyclohexenyl, cyclopentadienyl, indenyl and the like.

The term "cycloalkylidenyl", alone or in combination with any other term, refers to a stable cyclic hydrocarbon ring radical containing at least one exocyclic carbon-carbon double bond, wherein the cyclic hydrocarbon ring may be optionally fused, for example benzofused, with one to three cycloalkyl, aromatic, heterocyclic or heteroaromatic rings. The carbocycle may be attached at any cyclic carbon atom, which results in a stable structure. Where no number of carbon atoms is specified, a cycloalkylidenyl radical preferably has from 5–7 carbon atoms. Examples of cycloalkylidenyl radicals include, but are not limited to, cyclopentylidenyl, cyclohexylidenyl, cyclopentenylidenyl and the like.

The skilled practitioner would realize that certain groups could be classified either as cycloalkanes or as aryl groups. Examples of such groups include indanyl and tetrahydro naphthyl groups.

The term "monocycle" or "monocyclic" alone or in combination with any other term, unless otherwise defined herein, refers to a 5–7 membered ring system.

The term "bicycle" or "bicyclic" alone or in combination with any other term, unless otherwise defined herein, refers to a 6–11 membered ring system.

The term "tricycle" or "tricyclic" alone or in combination with any other term, unless otherwise defined herein, refers to a 11–15 membered ring system.

The terms "heterocyclyl" and "heterocycle", alone or in combination with any other term, unless otherwise defined herein, refers to a stable 5- to 15-membered mono-, bi-, or tricyclic, heterocyclic ring which is either saturated or partially unsaturated, but not aromatic, and which may be optionally fused, for example benzofused, with one to three cycloalkyl, aromatic, heterocyclic or heteroaromatic rings. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocycle may be attached at any endocyclic carbon or heteroatom which results in the creation of a stable structure.

Preferred heterocycles defined above include, for example, imidazolidinyl, indazolinolyl, perhydropyridazyl, pyrrolinyl, pyrrolidinyl, piperidinyl, pyrazolinyl, piperazinyl, morpholinyl, thiamorpholinyl, β-carbolinyl, thiazolidinyl, thiamorpholinyl sulfone, oxopiperidinyl, oxopyrroldinyl, oxoazepinyl, azepinyl, furazanyl, tetrahydropyranyl, tetrahydrofuranyl, oxathiolyl, dithiolyl, tetrahydrothiophenyl, dioxanyl, dioxolanyl, tetrahydrofurotetrahydrofuranyl, tetrahydropyranotetrahydrofuranyl, tetrahydrofurodihydrofuranyl, tetrahydropyranodihydrofuranyl, dihydropyranyl, dihydrofuranyl, dihydrofurotetrahydrofuranyl, dihydropyranotetrahydrofuranyl, sulfolanyl and the like.

The terms "heteroaryl" and "heteroaromatic" alone or in combination with any other term, unless otherwise defined herein, refers to a stable 3- to 7-membered monocyclic heterocyclic ring which is aromatic, and which may be optionally fused, for example, benzofused, with one to three cycloalkyl, aromatic, heterocyclic or heteroaromatic rings. Each heteroaromatic ring consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heteroaromatic ring may be attached at any endocyclic carbon or heteroatom which results in the creation of a stable, aromatic structure.

Preferred heteroaromatics defined above include, for example, benzimidazolyl, imidazolyl, quinolyl, isoquinolyl, indolyl, indazolyl, pyridazyl, pyridyl, pyrrolyl, pyrazolyl, pyrazinyl, quinoxolyl, pyranyl, pyrimidinyl, pyridazinyl, furyl, thienyl, triazolyl, thiazolyl, tetrazolyl, benzofuranyl, oxazolyl, benzoxazolyl, isoxazolyl, isothiazolyl, thiadiazolyl, thiophenyl, oxadiazolyl, oxatriazolyl, thiatriazolyl, dithiazolyl, dioxazolyl, oxathiazolyl, triazinyl and the like.

The term "halo" refers to a radical of fluorine, chlorine, bromine or iodine. Preferred halogen radicals include fluorine and chlorine.

In chemical formulas, parentheses are used herein to indicate 1) the presence of more than one atom or group bonded to the same atom or group; or 2) a branching point in a chain (i.e., the group or atom immediately before the open parenthesis is bonded directly to the group or atom immediately after the closed parenthesis). An example of the first use is "N(R$^1$)$_2$" denoting two R$^1$ groups bound to the nitrogen atom. An example of the second use is "—C(O)R$^1$" denoting an oxygen atom and a R$^1$ bound to the carbon atom, as in the following structure:

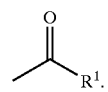

As used herein, "B" indicates a boron atom.

Those of skill in the art will realize that certain combinations of moiety choices for variables in the generic structures set forth throughout this application will produce chemically unstable or unfeasible compounds. Such compounds are not intended to be part of the present invention.

The present invention provides compounds that are useful as protease inhibitors, particularly as serine protease inhibitors, and more particularly as HCV NS3 protease inhibitors. As such, they act by interfering with the life cycle of the HCV virus and other viruses that are dependent upon a serine protease for proliferation. Therefore, these compounds are useful as antiviral agents.

According to one embodiment, the present invention provides a compound of the formula (I):

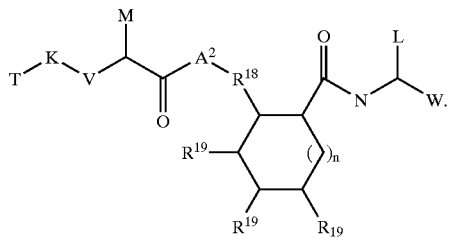

In these compounds W is selected from:

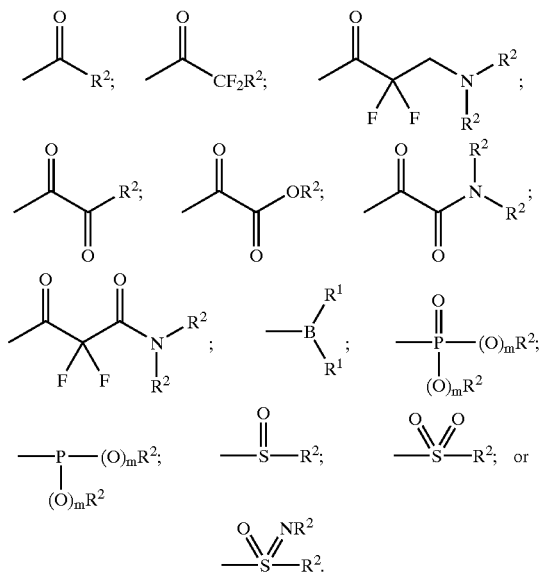

wherein m is 0 or 1.

Each $R^1$ is hydroxy, alkoxy, or aryloxy, or each $R^1$ is an oxygen atom and together with the boron, to which they are each bound, form a 5–7 membered ring, wherein the ring atoms are carbon, nitrogen, or oxygen.

Each $R^2$ is independently hydrogen, halo, alkyl, alkenyl, aryl, aralkyl, aralkenyl, cycloalkyl, cycloalkylalkyl, cycloalkenyl, cycloalkenylalkyl, heterocyclyl, heterocyclylalkyl, heterocyclylalkenyl, heteroaryl, or heteroaralkyl, or two $R^2$ groups, which are bound to the same nitrogen atom, form together with that nitrogen atom, a 5–7 membered monocyclic heterocyclic ring system; wherein any $R^2$ carbon atom is optionally substituted with J.

Each J is independently alkyl, aryl, aralkyl, alkoxy, aryloxy, aralkoxy, cycloalkyl, cycloalkoxy, heterocyclyl, heterocyclyloxy, heterocyclylalkyl, keto, hydroxy, amino, alkylamino, alkanoylamino, aroylamino, aralkanoylamino, carboxy, carboxyalkyl, carboxamidoalkyl, halo, cyano, nitro, formyl, acyl, sulfonyl, or sulfonamido and is optionally substituted with 1 to 3 $J^1$ groups.

Each $J^1$ is independently selected from alkyl, aryl, aralkyl, alkoxy, aryloxy, heterocyclyl, heterocyclyloxy, keto, hydroxy, amino, alkanoylamino, aroylamino, carboxy, carboxyalkyl, carboxamidoalkyl, halo, cyano, nitro, formyl, sulfonyl, or sulfonamido.

L is alkyl, alkenyl, or alkynyl, wherein any hydrogen bound to a carbon atoms is optionally substituted with halogen, and wherein any hydrogen or halogen atom bound to any terminal carbon atom is optionally substituted with sulfhydryl or hydroxy.

Each M is independently alkyl, cycloalkyl, aryl, aralkyl, heterocyclyl, heterocyclylalkyl, heteroaryl, or heteroaralkyl, and is optionally substituted by 1 to 3 J groups, wherein any alkyl carbon atom may be replaced by a heteroatom.

$R^{18}$ is a bond, $-N(R^{11})-$, or $-C(O)-$.

$R^{11}$ is hydrogen or $C_1-C_3$ alkyl.

Each $R^{19}$ is independently H or $R^{21}$-aryl, or 2 adjacent $R^{19}$ may be bound to one another to form a 5–7 membered aromatic ring, wherein any $R^{19}$ is optionally substituted with 1 to 4 independently selected J' groups. When 2 adjacent $R^{19}$ are bound to one another to form a 5–7 membered aromatic ring a bicyclic ring system is formed consisting of the aromatic ring shown in formula I and the aromatic ring formed by two adjacent $R^{19}$ groups. When $R^{19}$ is $R^{21}$-aryl, this optional substitution may occur on one or more carbon atoms of $R^{21}$ and/or on one or more ring atoms of said aryl. When 2 adjacent $R^{19}$ are bound to one another to form a 5–7 membered aromatic ring, the optional substitution may occur on one or more atoms of the resulting aromatic ring.

Each $R^{21}$ is independently $C_1-C_3$-straight or branched alkyl, $C_2-C_3$-straight or branched alkenyl, $O-(C_1-C_3)$-straight or branched alkyl, or $O-(C_2-C_3)$-straight or branched alkenyl.

n is 0 or 1.

The ring to which $R^{18}$ and $R^{19}$ are attached may be saturated, partially saturated, aromatic or fully unsaturated. Up to 3 carbon atoms that make up the ring to which $R^{18}$ and $R^{19}$ are attached are optionally replaced with a heteroatom which is independently selected from O, S, S(O), S(O)$_2$ or $N(R^{11})$.

$A^2$ is a bond or $-N(R^{11})-R^{17}(M)-R^{22}-$, wherein $R^{17}$ is $-CH-$ or $-N-$; and $R^{22}$ is $-C(O)-$ or $-S(O)_2-$.

V is a bond, $-CH(R)-$, $-O-$, $-S-$, or $-N(R^{11})-$.

K is a bond, $-O-$, $-S-$, $-C(O)-$, $-S(O)-$, $-S(O)_2-$, or $-S(O)NR^{11}-$.

T is $-R^{12}$, -alkyl-$R^{12}$, -alkenyl-$R^{12}$, -alkynyl-$R^{12}$, $-OR^{12}$, $-N(R^{12})_2$, $-C(O)R^{12}$, $-C(=NO-alkyl)R^{12}$ or

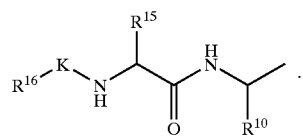

Each $R^{12}$ is independently selected from hydrogen, aryl, heteroaryl, cycloalkyl, heterocyclyl, cycloalkylidenyl, or heterocycloalkylidenyl, and is optionally substituted with 1 to 3 J groups; or a first $R^{12}$ and a second $R^{12}$, together with the nitrogen to which they are bound, form a mono- or bicyclic ring system optionally substituted by 1 to 3 J groups.

$R^{10}$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1 to 3 J groups.

$R^{15}$ is alkyl, cycloalkyl, aryl, aralkyl, heterocyclyl, heterocyclylalkyl, heteroaryl, heteroaralkyl, carboxyalkyl, or carboxamidoalkyl, and is optionally substituted with 1 to 3 J groups.

$R^{16}$ is hydrogen, alkyl, aryl, heteroaryl, cycloalkyl, or heterocyclyl.

Preferably, W is

[chemical structures showing various W groups including acyl-R², acyl-CF₂R², difluoroketone-CH₂-NR²₂, diketone-R², ester-OR², amide-NR²₂, difluoro-diketone-amide, phosphonate -P(=O)(O)ₘR², sulfoxide -S(O)R², sulfone -S(O)₂R², sulfoximine -S(=O)(=NR²)R²]

More preferably, W is

[structures: acyl-R²; diketone-amide -C(O)C(O)N(R²)₂; phosphonate]

Even more preferably, W is

[structures: -C(O)H; -C(O)CF₃; -C(O)CF₂CF₃; -C(O)C(O)NHR²]

wherein $R^2$ is aralkyl; or

[structure: -P(=O)(Oaryl)₂]

Most preferably, W is —C(O)H.

Preferably, J is alkyl, alkoxy, aryloxy, aryl, ralkyl, aralkoxy, halo, heteroaryl, cyano, amino, nitro, heterocyclyl, acyl, carboxy, carboxyalkyl, alkylamino, hydroxy, heterocyclylalkyl, aralkanoylamino, aroylamino, alkanoylamino, formyl or keto.

More preferably, J is t-butyl, methyl, trifluoromethyl, hydroxy, methoxy, ethoxy, trifluoromethoxy, carboxy, phenyl, benzyl, phenoxy, benzyloxy, fluoro, chloro, bromo, isoxazolyl, pyridinyl, piperidinyl, carboxymethyl, carboxyethyl, dialkylamino, morpholinylmethyl, phenylacetylamino, or acylamino.

Preferably, $J^1$ is alkoxy, alkyl, halo or aryl.

More preferably, $J^1$ is $C_{1-3}$ alkoxy, chloro, $C_{1-3}$ alkyl, or phenyl.

Preferably, L is alkyl, alkenyl, allyl, or propargyl.

More preferably, L is trihalomethyl, sulfhydryl or alkyl substituted with trihalomethyl, sulfhydryl, or hydroxy. Most preferably, L is —CH₂CH₃ or —CH₂CF₃.

Preferably, $R^2$ is H, fluorine, trifluoromethyl, alkyl, aryl, aralkyl, heteroaralkyl, heterocyclyl, or heterocyclylalkyl. More preferred is when $R^2$ is H.

Preferably, M is alkyl, heteroaralkyl, aryl, cycloalkylalkyl, aralkyl, or aralkyl, wherein one of the alkyl carbon atoms is replaced by O or S.

More preferably M is isopropyl, propyl, methyl, pyridylmethyl, benzyl, naphthylmethyl, phenyl, imidazolylmethyl, thiophenylmethyl, cyclohexylmethyl, phenethyl, benzylthiomethyl, or benzyloxyethyl. Most preferably, M is isopropyl.

Preferably, one $R^{19}$ is $R^{21}$-aryl and the other two $R^{19}$ are H or two $R^{19}$ are bound together to form an aromatic ring and the other $R^{19}$ is H. More preferred is when one $R^{19}$ is —O—($C_1$–$C_3$)-alkyl-aryl or the two $R^{19}$ bound together form a 6-membered aromatic ring. Most preferred is when one $R^{19}$ is —O-benzyl or the two $R^{19}$ bound together form phenyl.

Preferably, $R^{18}$ is —N($R^{11}$)—. More preferably, $R^{18}$ is —N(H)— or —N(CH₃)—.

Preferably, the ring to which $R^{18}$ and $R^{19}$ are attached is aromatic.

It is preferred that $A^2$ be a bond or —N($R^{11}$)—C(M)—C(O)—. More preferred is when $A^2$ is a bond or —N(H)—C(M)—C(O)—, wherein M is isopropyl.

Preferably, V is —N($R^{11}$)—. More preferably, V is —NH—.

Preferably, K is —C(O)— or —S(O)₂—. More preferably, K is —C(O)—

Preferably, T is —$R^{12}$, -alkyl-$R^{12}$, -alkenyl-$R^{12}$, —O$R^{12}$, —N($R^{12}$)₂, —C(=NO-alkyl)-$R^{12}$, or

[structure: $R^{16}$-K-N(H)-CH($R^{15}$)-C(O)-N(H)-CH($R^{10}$)-]

More preferably, T is —$R^{12}$ or -alkyl-$R^{12}$.

Preferably, $R^{12}$ is aryl or heteroaryl and is optionally substituted by 1–3 J groups. More preferably, $R^{12}$ is naphthyl, pyrazinyl, or pyridyl, any of which is optionally substituted with a hydroxy group Preferably, $R^{10}$ is alkyl substituted with carboxy. More preferably, $R^{10}$ is $C_{1-3}$ alkyl substituted with carboxy.

Preferably, $R^{15}$ is alkyl substituted with carboxy. More preferably, $R^{15}$ is $C_{1-3}$ alkyl substituted with carboxy.

The most preferred compounds of this invention are listed in Table 1, below.

TABLE 1

Preferred Compounds of the formula:

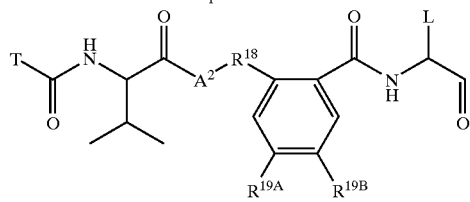

| Compound | T | A² | R¹⁸ | R¹⁹ᴬ | R¹⁹ᴮ | L |
|---|---|---|---|---|---|---|
| 101 | pyrazinyl | H₃C CH₃ / HN-CH-C(O) | —N(H)— | H | O-benzyl | —CH₂CH₃ |
| 102 | pyrazinyl | H₃C CH₃ / HN-CH-C(O) | —N(H)— | H | O-benzyl | —CH₂CF₃ |
| 103 | pyrazinyl | H₃C CH₃ / HN-CH-C(O) | —N(CH₃)— | H | O-benzyl | —CH₂CH₃ |
| 104 | 2-hydroxynaphthyl | bond | —N(H)— | H | O-benzyl | —CH₂CH₃ |
| 105 | 6-hydroxypyridin-3-yl | bond | —N(H)— | H | O-benzyl | —CH₂CH₃ |
| 106 | hydroxynaphthyl | bond | —N(H)— | H | O-benzyl | —CH₂CH₃ |
| 107 | pyrazinyl | H₃C CH₃ / HN-CH-C(O) | —N(H)— | H | O-3,4-dichlorobenzyl | —CH₂CH₃ |

TABLE 1-continued

Preferred Compounds of the formula:

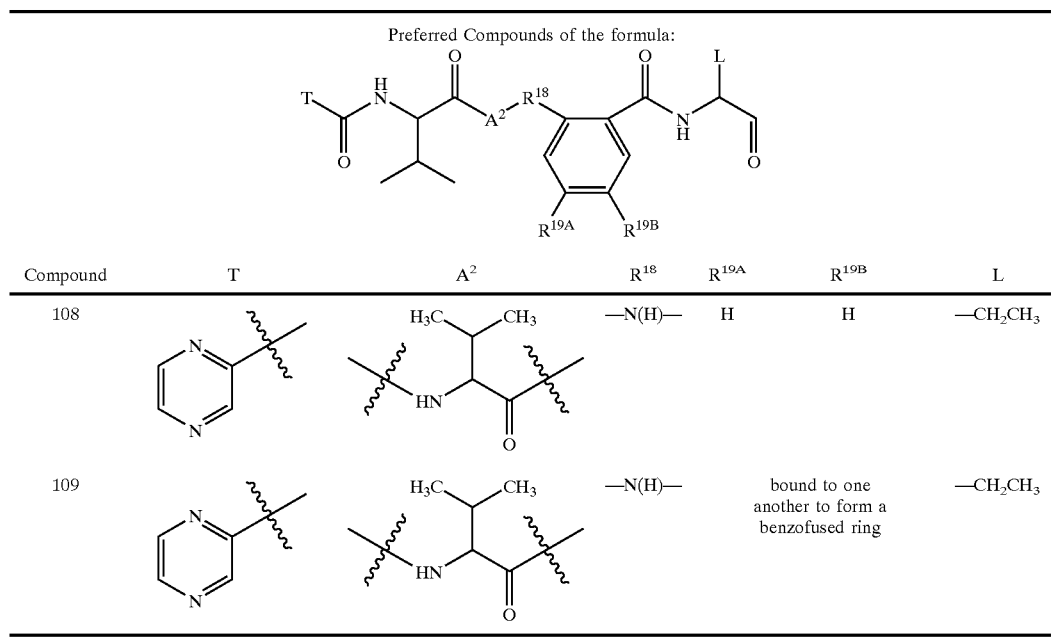

| Compound | T | A² | R¹⁸ | R¹⁹ᴬ | R¹⁹ᴮ | L |
|---|---|---|---|---|---|---|
| 108 | pyrazinyl | H₃C-CH(CH(CH₃))-HN-C(O)- | —N(H)— | H | H | —CH₂CH₃ |
| 109 | pyrazinyl | H₃C-CH(CH(CH₃))-HN-C(O)- | —N(H)— | bound to one another to form a benzofused ring | | —CH₂CH₃ |

This invention anticipates that many active-site directed inhibitors of the NS3 protease may be peptidomimetic in nature and thus may be designed from the natural substrate. Therefore, preferred substituents in peptidomimetic inhibitors of this invention include those which correspond to the backbone or side chains of naturally occurring substrates or synthetic substrates with high affinity for the enzyme (low $K_m$).

The skilled practitioner would realize that some certain groups could be classified either as heterocycles or heteroaromatics, depending on the point of attachment.

The compounds of this invention may contain one or more asymmetric carbon atoms and thus may occur as racemates and racemic mixtures, single enantiomers, diastereomeric mixtures and individual diastereomers. All such isomeric forms of these compounds are expressly included in the present invention. Each stereogenic carbon may be of the R or S configuration. Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic or prophylactic administration to a mammal or for use in affinity chromatography applications). Typically, such compounds are stable at a temperature of 40° C. or less, in the absence of moisture or other chemically reactive conditions, for at least a week.

The compounds of this invention may be synthesized using conventional techniques. Advantageously, these compounds are conveniently synthesized from readily available starting materials.

As used herein, the compounds of this invention are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention.

Accordingly, this invention also provides prodrugs of the compounds of this invention, which are derivatives that are designed to enhance biological properties such as oral absorption, clearance, metabolism or compartmental distribution. Such derivations are well known in the art.

As the skilled practitioner realizes, the compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

The term "protected" refers to when the designated functional group is attached to a suitable chemical group (protecting group). Examples of suitable amino protecting groups and protecting groups are described in T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); L. Paquette, ed. *Encyclopedia of Reagents for Organic Synthesis*, John Wiley and Sons (1995) and are exemplified in certain of the specific compounds used in this invention.

Particularly favored derivatives and prodrugs are those that increase the bioavailability of the compounds of this invention when such compounds are administered to a mammal (e.g., by allowing an orally administered compound to be more readily absorbed into the blood), have more favorable clearance rates or metabolic profiles, or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formula (I).

Pharmaceutically acceptable salts of the compounds of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphtha-lenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., calcium and magnesium), salts with organic bases, such as dicyclohexylamine salts, N-methyl-D-glucamine, salts with amino acids such as arginine and lysine, ammonium and N-$(C_{1-4}$ alkyl$)_4^+$ salts.

This invention also envisions the quaternization of any basic nitrogen-containing groups of the compounds disclosed herein with such agents as lower alkyl halides, such as methyl, ethyl, propyl, and butyl chloride, bromides and iodides; dialkyl sulfates, such as dimethyl, diethyl, dibutyl and diamyl sulfates, long chain halides such as decyl, lauryl, myristyl and stearyl chlorides, bromides and iodides, aralkyl halides, such as benzyl and phenethyl bromides and others. Water or oil-soluble or dispersible products may be obtained by such quaternization.

In general, compounds of formula (I) are obtained via methods illustrated in the Examples. As can be appreciated by the skilled artisan however the synthetic schemes set forth herein are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds.

Without being bound by theory, we believe that the compounds of this invention interact either covalently or noncovalently with the active site of the HCV NS3 protease and other serine proteases, inhibiting the ability of such an enzyme to cleave natural or synthetic substrates. Noncovalent interactions are advantageous in that they impart relatively greater specificity of inhibition and will not inhibit other undesirable targets, e.g. cysteine proteases. These compounds will therefore have a greater therapeutic index when administered to mammals than covalent protease inhibitors, which can interact with a wide range of proteases and cause undesirable toxic effects. In contrast, covalent interactions are advantageous in that they impart greater inhibitory potency allowing lower doses may be administered and thus ameliorating any lack of specificity problems.

The novel compounds of the present invention are excellent inhibitors of proteases, particularly serine proteases, and more particularly HCV NS3 protease inhibitors. Accordingly, these compounds are capable of targeting and inhibiting proteases, particularly serine proteases, and more particularly HCV NS3 proteases. As such, these compounds interfere with the life cycle of viruses, including HCV and are thus useful as antiviral agents. Inhibition can be measured by various methods such as the methods of Example 3.

The term "antiviral agent" refers to a compound or drug which possesses viral inhibitory activity. Such agents include reverse transcriptase inhibitors (including nucleoside and non-nucleoside analogs) and protease inhibitors. Preferably the protease inhibitor is a HCV protease inhibitor.

The term "treating" as used herein refers to the alleviation of symptoms of a particular disorder in a patient or the improvement of an ascertainable measurement associated with a particular disorder. As used herein, the term "patient" refers to a mammal, including a human.

Thus, according to another embodiment this invention provides pharmaceutical compositions comprising a compound of formula (I) or a pharmaceutically acceptable salt thereof; an additional agent selected from, but not including, an immunomodulatory agent, such as α-, β-, or γ-interferon; other antiviral agents, such as ribavarin or amantadine; other inhibitors of HCV protease; inhibitors of other targets in the HCV life cycle such as helicase, polymerase, or metalloprotease; or combinations thereof and any pharmaceutically acceptable carrier, adjuvant or vehicle. An alternate embodiment provides compositions comprising a compound of formula (I) or a pharmaceutically acceptable salt thereof; and a pharmaceutically acceptable carrier, adjuvant or vehicle. Such composition may optionally comprise an additional agent selected from an immunomodulatory agent, such as α-, β-, or γ-interferon; other antiviral agents, such as ribavarin; other inhibitors of HCV protease; inhibitors of the HCV helicase; or combinations thereof.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as dα-tocopherol, polyethyleneglycol 1000 succinate, or TPGS, surfactants used in pharmaceutical dosage forms such as Tweens or other similar polymeric delivery matrices, serum proteins, such as human serum albumin, gelatin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polylacetic acid, ployacetic polyglycollic acid, citric acid, cellulose-based substances, such as HPC and HPMC, polyethylene glycol, sodium carboxymethylcellulose, polyacrylates, waxes, polyethylene-polyoxypropylene-block polymers, polyethylene glycol, wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of formula (I).

The pharmaceutical compositions of this invention may be administered orally, parenterally, by inhalation spray, topically, rectally, nasally, buccally, vaginally or via an implanted reservoir. We prefer oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension.

This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant such as those described in Pharmacopeia Helvetica (Ph. Helv.) or a similar alcohol, or carboxymethyl cellulose or similar dispersing agents which are commonly used in the formulation of pharmaceutically acceptable dosage forms such as emulsions and/or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, and aqueous suspensions and solutions. In the case of tablets for oral use, carriers which are commonly used include lactose, corn starch, dicalcium phosphate and microcrystalline cellulose (Avicel). Lubricating agents, such as magnesium stearate and talc, are also typically added. For oral administration in a capsule form, useful diluents include lactose, dried corn starch and TPGS, as well as the other diluents used in tablets. For oral administration in a soft gelatin capsule form (filled with either a suspension or a solution of a compound of this invention), useful diluents include PEG400, TPGS, propylene glycol, Labrasol, Gelucire, Transcutol, PVP and potassium acetate. When aqueous suspensions are administered orally, the active ingredient is combined with emulsifying and suspending agents, such as sodium CMC, methyl cellulose, pectin and gelatin. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax, gelatin, glycerin and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax, stearic acid, cetyl stearate, cetyl alcohol, lanolin, magnesium hydroxide, kaolin and water. Alternatively, the pharmaceutical composition can be formulated with a suitable lotion or cream containing the active compound suspended or dissolved in a carrier. Suitable carriers include, but are not limited to, mineral oil, sorbitan monostearate, polysorbate 60, cetyl esters, wax, cetyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

Dosage levels of between about 0.01 and about 100 mg/kg body weight per day, preferably between about 0.5 and about 75 mg/kg body weight per day of the protease inhibitor compounds described herein are useful in a monotherapy for the prevention and treatment of antiviral, particularly anti-HCV mediated disease. Typically, the pharmaceutical compositions of this invention will be administered from about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

When the compositions of this invention comprise a combination of a compound of formula (I) and one or more additional therapeutic or prophylactic agents, both the compound and the additional agent should be present at dosage levels of between about 10 to 100%, and more preferably between about 10 to 80% of the dosage normally administered in a monotherapy regimen.

According to one embodiment, the pharmaceutical compositions of this invention comprise an additional immunomodulatory agent. Examples of additional immunomodulatory agents include, but are not limited to, α-, β-, and δ-interferons.

According to an alternate embodiment, the pharmaceutical compositions of this invention may additionally comprise an anti-viral agent. Examples of anti-viral agents include, ribavirin and amantadine.

According to another alternate embodiment, the pharmaceutical compositions of this invention may additionally comprise other inhibitors of HCV protease.

According to yet another alternate embodiment, the pharmaceutical compositions of this invention may additionally comprise an inhibitor of other targets in the HCV life cycle, such as helicase, polymerase, or metalloprotease.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level, treatment should cease. Patients may, however, require intermittent treatment on a long-term basis upon any recurrence of disease symptoms.

As the skilled artisan will appreciate, lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the infection, the patient's disposition to the infection and the judgment of the treating physician.

When these compounds or their pharmaceutically acceptable salts are formulated together with a pharmaceutically acceptable carrier, the resulting composition may be administered in vivo to mammals, such as man, to inhibit serine proteases, particularly HCV NS3 protease or to treat or prevent viral infection, particularly HCV virus infection. Such treatment may also be achieved using the compounds of this invention in combination with agents which include, but are not limited to: immunomodulatory agents, such as α-, β-, or γ-interferons; other antiviral agents such as ribavirin, amantadine; other inhibitors of HCV NS3 protease; inhibitors of other targets in the HCV life cycle such as helicase, polymerase, metalloprotease, or internal ribosome entry; or combinations thereof. These additional agents may be combined with the compounds of this invention to create a single dosage form. Alternatively these additional agents may be separately administered to a mammal as part of a multiple dosage form.

Accordingly, another embodiment of this invention provides methods of inhibiting serine protease activity in mammals by administering a compound of the formula (I), wherein the substituents are as defined above. Preferably, the serine protease is HCV NS3.

In an alternate embodiment, the invention provides methods of inhibiting HCV or HCV NS3 activity in a mammal comprising the step of administering to said mammal, a compound of formula (I), wherein the substituents are as defined above.

In an alternate embodiment, this invention provides methods of decreasing serine protease activity in a mammal comprising the step of administrating to said mammal any of the pharmaceutical compositions and combinations described above. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle. Such additional agent may be administered to the mammal prior to, concurrently with, or following the administration of the HCV inhibitor composition.

In a preferred embodiment, these methods are useful in decreasing HCV NS3 protease activity in a mammal. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle such as helicase, polymerase, or metalloprotease. Such additional agent may be administered to the mammal prior to, concurrently with, or following the administration of the compositions of this invention.

In an alternate preferred embodiment, these methods are useful for inhibiting viral replication in a mammal. Such methods are useful in treating or preventing, for example, viral diseases, such as HCV. If the pharmaceutical composition comprises only a compound of this invention as the active component, such methods may additionally comprise the step of administering to said mammal an agent selected from an immunomodulatory agent, an antiviral agent, a HCV protease inhibitor, or an inhibitor of other targets in the HCV life cycle. Such additional agent may be administered to the mammal prior to, concurrently with, or following the administration of the composition according to this invention.

The compounds set forth herein may also be used as laboratory reagents. The compounds of this invention may also be used to treat or prevent viral contamination of materials and therefore reduce the risk of viral infection of laboratory or medical personnel or patients who come in contact with such materials. These materials include, but are not limited to, biological materials, such as blood, tissue, etc; surgical instruments and garments; laboratory instruments and garments; and blood collection apparatuses and materials.

In order that this invention be more fully understood, the following examples are set forth. These examples are for the purpose of illustration only and are not to be construed as limiting the scope of the invention in any way.

General Materials and Methods

Compounds 101 through 109 were prepared using the generic synthesis scheme 1, depicted below. Synthesis of specific compounds are described in the following examples.

The correct $(M+H)^+$ and/or $(M+Na)^+$ molecular ions for all compounds as set forth in Table 2 were obtained by either matrix-assisted laser desorption mass spectrometry (Kratos MALDI I) or by electro spray mass spectrometry (MICROMASS Quatro II).

Numerous amino acids for use in the synthesis of peptidyl and peptidomimetic compounds of this invention may be purchased commercially from, for instance, Sigma Chemical Company or Bachem Feinchemikalien AG (Switzerland). Amino acids that are not commercially available can be made by known synthetic routes ("Kinetic Resolution of Unnatural and Rarely Occurring Amino Acids: Enantioselective Hydrolysis of N-Acyl Amino Acids Catalyzed by Acylase I", Chenault, H. K. et. al., *J. Am. Chem. Soc.* 111, 6354–6364 (1989) and references cited therein; "Synthesis of β-γ-Unsaturated Amino Acids by the Strecker Reaction, Greenlee, W. J., *J. Org. Chem.* 49, 2632–2634 (1984); "Recent Stereoselective Synthetic Approaches to Beta-amino Acids", Cole, D. *Tetrahedron* 50: 9517 (1994); "The Chemistry of Cyclic Alpha Imino Acids", Mauger, A.B; Volume 4 of "Chemistry and Biochemistry of Amino Acids, Peptides, and Proteins", Weinstein, B. editor, Marcel Dekker (1977); "Recent Progress in the Synthesis and Reactions of Substituted Piperidines", Org. Prep. Procedure int. 24, 585–621 (1992), all of which are incorporated herein by reference).

Certain compounds of formula (I) may be synthesized from amino acids by procedures which are well known in the art of peptide and organic chemical synthesis. Examples of such syntheses are generally set forth in Bodanszky and Bodanszky, "The Practice of Peptide Synthesis", Springer-Verlag, Berlin, Germany (1984), "The Peptides", Gross and Meinhofer, eds.; Academic Press, 1979, Vols. I–III, and Stewart, J. M. and Young, J. D., "Solid Phase Peptide Synthesis, Second Edition", Pierce Chemical Company, Rockford, Ill. (1984); and "Recent Advances in the Generation of Molecular Diversity", Moos, W. H., Green, G. D. and Pavia, M. R. in "Annual Reports in Medicinal Chemistry, Vol. 28" pp. 315–324; Bristol, J. A., ed.; Academic Press, San Diego, Calif. (1993), all of which are incorporated herein by reference.

Typically, for solution phase synthesis of peptides, the α-amine of the amino acid to be coupled is protected by a urethane such as Boc, Cbz, Fmoc or Alloc while the free carboxyl is activated by reaction with a carbodiimide such as DCC, EDC, or DIC, optionally in the presence of a catalyst such as HOBT, HOAt, HOSu, or DMAP. Other methods, which proceed through the intermediacy of activated esters, acid halides, enzyme-activated amino acids and anhydrides including phosphonium reagents such as BOP, Py-BOP, N-carboxy-anhydrides, symmetrical anhydrides, mixed carbonic anhydrides, carbonic-phosphinic and carbonic-phosphoric anhydrides, are also suitable. After the peptide has been formed, protecting groups may be removed by methods described in the references listed above, such as by hydrogenation in the presence of a palladium, platinum or rhodium catalyst, treatment with sodium in liquid ammonia, hydrochloric, hydrofluoric, hydrobromic, formic, trifluoromethanesulfonic, or trifluoroacetic acid, secondary amines, fluoride ion, trimethylsilyl halides including bromide and iodide, or alkali. Automation of the synthetic process, using techniques such as those set forth above, can be accomplished by use of commercially available instrumentation, including but not limited to the Advanced Chemtech 357 FBS and 496 MOS; Tecan CombiTec, and Applied Biosystems 433A among others. Specific application of these methods and their equivalents, depending upon the target compound, will be apparent to those skilled in the art. Modifications of chemical processes and choice of instrumentation is within the skill of the ordinary practitioner.

Although some of the schemes depicted below indicate particular stereochemistry for certain groups, it should be apparent to those of skill in the art that the synthesis schemes may be modified to allow for the use of those certain groups having the opposite stereochemistry. Therefore, the indication of stereochemistry in these scheme is not intended to limit the depicted synthesis to any particular stereochemistry of any intermediate or final product.

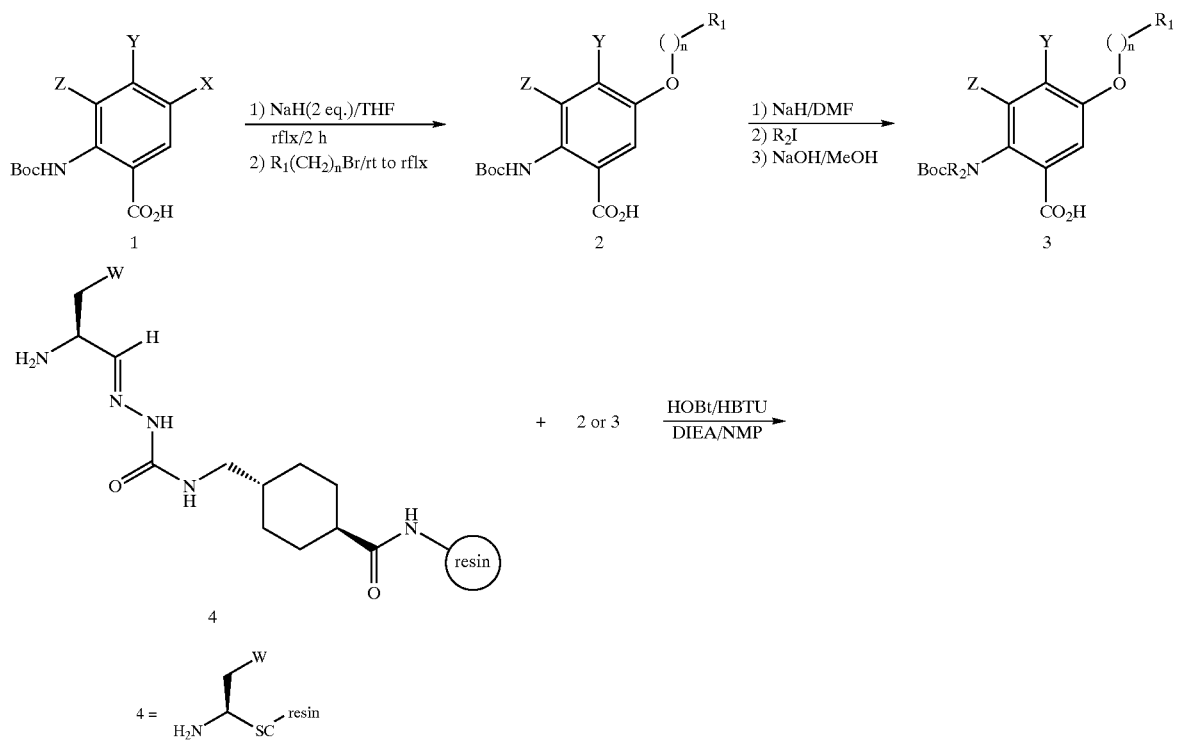

SCHEME 1
General Syntheses for the Anthranilic Acids

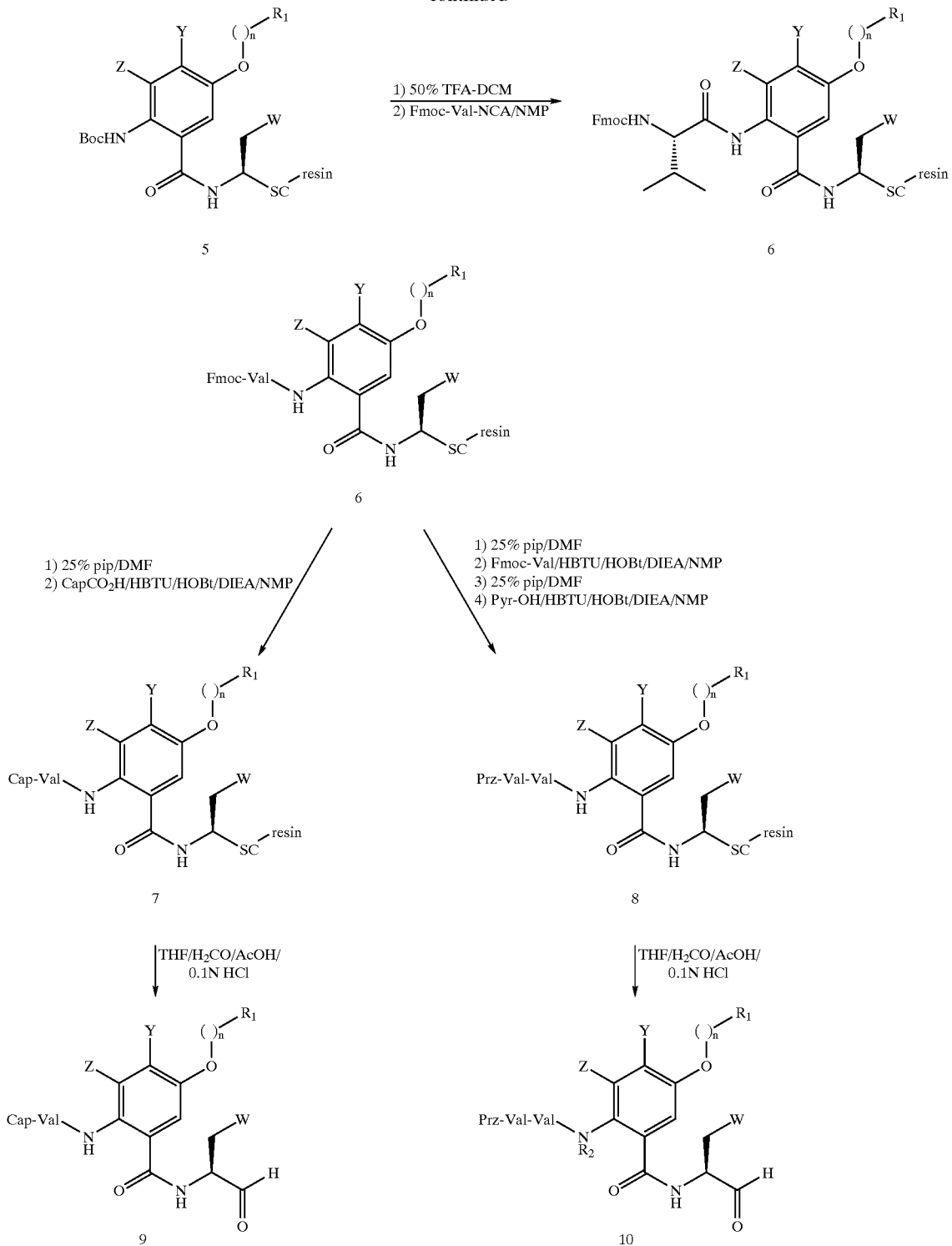

EXAMPLE 1

Synthesis of Compound 101

Synthesis of 2. To a solution of Boc-5-hydroxyanthranilic acid (1) (1.5 g, 5.8 mmol) in 45 mL of anhydrous THF at room temperature was added portionwise, sodium hydride (581 mg, 14.5 mmol). The mixture was stirred and heated to reflux for 2 hours and cooled to room temperature. Benzyl bromide (691 mL, 5.8 mmol) was then added and the reaction mixture was heated to reflux for 1.5 hours, cooled to room temperature and stirred overnight. The reaction was quenched with ice-water (40 mL) and carefully acidified to pH 3 with HCl 2N. Extraction with ethyl acetate (100 mL) followed by a water (50 mL) and a brine (40 mL) wash gave, after drying over $Na_2SO_4$ and concentration in vacuo, a solid residue. Flash chromatography of the crude mixture (10% methanol-90% dichloromethane) provided 1.42 g (70%) of the desired product 2.

Synthesis of 4. 4-Methyl Benzhydrylamine resin (1.05 mmol/g, 20.0 g) was placed in a sintered glass funnel and washed with dimethylformamide (3×75 mL), 10% (v/v) diisopropylethylamine (DIEA) in dimethylformamide (2×75 mL) and finally with dimethylformamide (4×75 mL). Sufficient dimethylformamide was added to the resin to obtain a slurry followed by:

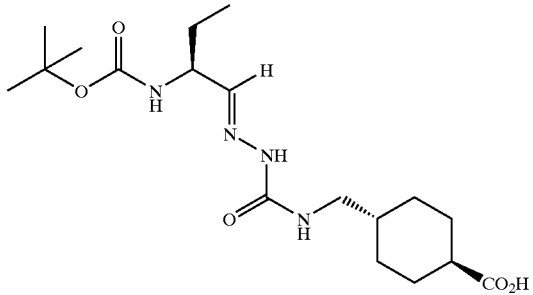

(8.0 g, 20.8 mmol, prepared from (2S) 2-(t-Butyloxycarbonylamino)-butyraldehyde according to A. M. Murphy et. al. *J. Am. Chem. Soc.*, 114, 3156–3157 (1992)), 1-hydroxybenzotriazole hydrate (HOBT.H2O; 3.22 g, 21.0 mmol), O-benzotriazole-N,N,N',N'-tetramethyluronium hexafluorophosphate (HBTU; 8.0 g, 21.0 mmol), and DIEA (11.0 mL, 63 mmol). The reaction mixture was agitated overnight at room temperature using a wrist arm shaker. The resin was isolated on a sintered glass funnel by suction filtration and washed with dimethylformamide (3×75 mL). Unreacted amine groups were then capped by reacting the resin with 20% (v/v) acetic anhydride/dimethylformamide (2×50 mL) directly in the funnel (10 min/wash). The resin was washed with dimethylformamide (3×75 mL) and dichloromethane (3×75 mL) prior to drying overnight in vacuo to yield an intermediate resin (26.3 g, 81% yield).

The t-Boc protecting group was removed from the intermediate resin using the Advanced ChemTech 396 Multiple Peptide synthesizer by the following procedure. The intermediate resin (0.05 mmol) was swelled by washing with dichloromethane (3×1 mL) followed by cleavage of the t-Boc protecting group with 50% (v/v) TFA/dichloromethane (1.0 mL) for 10 minutes (with shaking) followed by fresh reagent (1 mL) for 30 minutes. The resin was then washed with dichloromethane (3×1 ml), followed by DMF (3×1 mL), then 10% DIEA/dimethylformamide (v/v) (2×1 mL), and finally with N-methypyrrolidone (3×1 mL) to yield resin 4.

Synthesis of 5. Resin 4 (554 mg, 0.36 mmol) was placed in a Nalgene syringe equipped with a filter at the bottom and coupled to 2 (251 mg, 0.72 mmol) with HOBt (110 mg, 0.72 mmol), HBTU (273 mg, 0.72 mmol) and DIEA (376 mL, 2.16 mmol) in 4 mL of NMP (with shaking) for 72 hours. The solvent was removed by suction and the resin washed sequentially with NMP (3×4 mL) and dichloromethane (3×4 mL) to provide resin 5.

Synthesis of 6. The t-Boc protecting group was removed from the resin 5 (in the Nalgene syringe) with 50% (v/v) TFA/dichloromethane (6 mL) for 20 min. (with shaking). The resin was washed with dichloromethane (3×5 mL), followed by 10% DIEA/dichloromethane (3×5 mL) and finally with dichloromethane (3×5 mL). To the resulting resin was added Fmoc-valine-N-carboxy anhydride (526 mg, 1.44 mmol) and 6 mL of NMP. The reaction mixture was agitated for 72 hours at room temperature and the solvent was removed by suction. The resin 6 was washed sequentially with NMP (3×5 mL) and dichloromethane (3×5 mL) and used directly for the next step.

Synthesis of 8. This compound was prepared from resin 6 (0.1 mmol) using an Applied Biosystems Model 433A Peptide synthesizer. $N^{\alpha}$-Fmoc-protected amino acid and pyrazine-2-carboxylic acid were added sequentially to resin 6 with standard coupling cycles using HBTU with HOBt as coupling agents in NMP to yield resin 8.

Syntheses of Compound 101. The aldehyde was cleaved from the resin 8 by treatment with 10 mL of a solution of THF/30% formalin/AcOH/Q.1N HCl 5:1:1:1 (v:v:v:v) for 1 hour at room temperature. After washing the resin with cleavage reagent (5 mL), the combined filtrates were diluted with water (15 mL) and 5 mL of that mixture was purified by RP-HPLC with a Waters DeltaPak 300 A C18 column (15 m, 30×300 mm) eluting with a linear acetonitrile gradient containing 0.1% TFA (v/v) over 45 min. at 20 mL/min. Fractions containing the desired product were pooled and lyophilized to provide 101. M+H=617.3.

EXAMPLE 2

Synthesis of Compound 102

Intermediates 1 through 4 were prepared as in Example 1.

Synthesis of 5. Resin 4 ($W=CF_3$)(1.2 g, 0.384 mmol) was placed in a Nalgene syringe equipped with a filter at the bottom and coupled to 2 (267 mg, 0.768 mmol) with HOBt (118 mg, 0.768 mmol), HBTU (291 mg, 0.768 mmol) and DIEA (401 mL, 2.3 mmol) in 4 mL of NMP (with shaking) for 72 hours. The solvent was removed by suction and the resin washed sequentially with NMP (3×4 mL) and dichloromethane (3×4 mL) to provide resin 5.

Synthesis of 6. The t-Boc protecting group was removed from the resin 5 (in the Nalgene syringe) with 50% (v/v) TFA/dichloromethane (6 mL) for 20 minutes (with shaking). The resin was washed with dichloromethane (3×5 mL), followed by 10% DIEA/dichloromethane (3×5 mL) and finally with dichloromethane (3×5 mL). To the resulting resin was added Fmoc-valine-N-carboxy anhydride (562 mg, 1.54 mmol) and 8 mL of NMP. The reaction mixture was agitated for 72 hours at room temperature and the solvent was removed by suction. The resin 6 was washed sequentially with NMP (3×6 mL) and dichloromethane (3×6 mL) and used directly for the next step.

Synthesis of 8. This compound was prepared from resin 6 (0.1 mmol) using an Applied Biosystems Model 433A Peptide synthesizer. Na-Fmoc-protected amino acid and pyrazine-2-carboxylic acid were added sequentially to resin 6 with standard coupling cycles using HBTU with HOBt as coupling agents in NMP to yield resin 8.

Syntheses of 102. The aldehyde was cleaved from the resin 8 by treatment with 10 mL of a solution of THF/30% formalin/AcOH/0.1N HCl 5:1:1:1 (v:v:v:v) for 1 hour at room temperature. After washing the resin with cleavage reagent (5 mL), the combined filtrates were diluted with water (15 mL) and 5 mL of that mixture was purified by RP-HPLC with a Waters DeltaPak 300 A C18 column (15 m, 30×300 mm) eluting with a linear acetonitrile gradient containing 0.1% TFA (v/v) over 45 min. at 20 mL/min. Fraction containing the desired product were pooled and lyophilized to provide 102. M+H=671.2.

EXAMPLE 3

Synthesis of Compound 103

Synthesis of 3 ($R_2$=Me). To a solution of 2 (350 mg, 0.001 mol) in 10 mL of anhydrous DMF at room temperature was added, portionwise, NaH (100 mg, 0.0025 mol). The mixture was stirred for 40 minutes, then methyl iodide (0.175 mL, 0.0028 mol) was added and the reaction mixture was stirred overnight. The reaction was quenched with water and extracted with ethyl acetate. The organic phase was dried ($Na_2SO_4$) and concentrated in vacuo to provide 335 mg (89%) of an oil that was used directly for the next step.

To a solution of the above oil (335 mg, 0.0089 mol) in 8 mL of methanol room temperature was added 2.2 mL of 2N NaOH. The reaction was stirred overnight at room temperature after which the methanol was removed under vacuum. The resulting aqueous phase was diluted with water then slowly acidified to pH 3 with 1N HCl. The aqueous phase was extracted with ethyl acetate and the organic phase dried ($Na_2SO_4$) and concentrated in vacuo to give 300 mg (93%) of 3 that was used directly for the next step.

Synthesis of 6. The t-Boc protecting group was removed from the resin 5 (in the Nalgene syringe) with 50% (v/v) TFA/dichloromethane (6 mL) for 20 min. (with shaking). The resin was washed with dichloromethane (3×5 mL), followed by 10% DIEA/dichloromethane (3×5 mL) and finally with dichloromethane (3×5 mL). To the resulting resin was added Fmoc-valine-N-carboxy anhydride (606 mg, 1.66 mmol) and 10 mL of NMP. The reaction mixture was agitated for 72 hours at room temperature and the solvent was removed by suction. The resin 6 was washed sequentially with NMP (3×6 mL) and dichloromethane (3×6 mL) and used directly for the next step.

Synthesis of 8. This compound was prepared from resin 6 (0.1 mmol) using an Applied Biosystems Model 433A Peptide synthesizer. $N_a$-Fmoc-protected amino acid and pyrazine-2-carboxylic acid were added sequentially to resin 6 with standard coupling cycles using HBTU with HOBt as coupling agents in NMP to yield resin 8.

Syntheses of 103. The aldehyde was cleaved from the resin 8 by treatment with 10 mL of a solution of THF/30% formalin/AcOH/0.1N HCl 5:1:1:1 (v:v:v:v) for 1 hour at room temperature. After washing the resin with cleavage reagent (5 mL), the combined filtrates were diluted with water (15 mL) and 5 mL of that mixture was purified by RP-HPLC with a Waters DeltaPak 300 A C18 column (15 m, 30×300 mm) eluting with a linear acetonitrile gradient containing 0.1% TFA (v/v) over 45 min. at 20 mL/min. Fraction containing the desired product were pooled and lyophilized to provide 103. M+H=631.3.

EXAMPLE 4

Synthesis of Compound 104

Intermediates 1 through 6 were prepared as in Example 1.

Synthesis of 7. This compound was prepared from resin 6 (0.1 mmol) using an Applied Biosystems Model 433A Peptide synthesizer. 2-Hydroxynaphthoic acid was added to resin 6 with standard coupling cycles using HBTU with HOBt as coupling agents in NMP to yield resin 7.

Syntheses of 104. The aldehyde was cleaved from the resin 7 by treatment with 3 mL of a solution of THF/30% formalin/AcOH/0.1N HCl 5:1:1:1 (v:v:v:v) for 1 hour at room temperature. After washing the resin with cleavage reagent (1.5 mL), the combined filtrates were diluted with water (4.5 mL) and 5 mL of that mixture was purified by RP-HPLC with a Waters DeltaPak 300 A C18 column (15 m, 30×300 mm) eluting with a linear acetonitrile gradient containing 0.1% TFA (v/v) over 45 min. at 20 mL/min. Fraction containing the desired product were pooled and lyophilized to provide 104. M+H=582.2.

EXAMPLE 5

Synthesis of Compound 105

Intermediates 1 through 6 were prepared as in Example 1.

Synthesis of 7. This compound was prepared from resin 6 (0.1 mmol) using an Applied Biosystems Model 433A Peptide synthesizer. 2-Hydroxy-4-nicotinic acid was added to resin 6 with standard coupling cycles using HBTU with HOBt as coupling agents in NMP to yield resin 7.

Syntheses of 105. The aldehyde was cleaved from the resin 8 by treatment with 3 mL of a solution of THF/30% formalin/AcOH/0.1N HCl 5:1:1:1 (v:v:v:v) for 1 hour at room temperature. After washing the resin with cleavage reagent (1.5 mL), the combined filtrates were diluted with water (4.5 mL) and 5 mL of that mixture was purified by RP-HPLC with a Waters DeltaPak 300 A C18 column (15 m, 30×300 mm) eluting with a linear acetonitrile gradient containing 0.1% TFA (v/v) over 45 min. at 20 mL/min. Fraction containing the desired product were pooled and lyophilized to provide 105. M+H=533.2.

EXAMPLE 6

Synthesis of Compound 106

Intermediates 1 through 6 were prepared as in Example 1.

Synthesis of 7. This compound was prepared from resin 6 (0.1 mmol) using an Applied Biosystems Model 433A Peptide synthesizer. 6-Hydroxynaphthoic acid was added to resin 6 with standard coupling cycles using HBTU with HOBt as coupling agents in NMP to yield resin 7.

Syntheses of 106. The aldehyde was cleaved from the resin 8 by treatment with 3 mL of a solution of THF/30% formalin/AcOH/0.1N HCl 5:1:1:1 (v:v:v:v) for 1 hour at room temperature. After washing the resin with cleavage reagent (1.5 mL), the combined filtrates were diluted with water (4.5 mL) and 5 mL of that mixture was purified by RP-HPLC with a Waters DeltaPak 300 A C18 column (15 m, 30×300 mm) eluting with a linear acetonitrile gradient containing 0.1% TFA (v/v) over 45 min. at 20 mL/min. Fraction containing the desired product were pooled and lyophilized to provide 106. M+H=582.2.

EXAMPLE 7

Synthesis of Compound 107

Synthesis of 2. To a solution of Boc-5-hydroxyanthranilic acid (1) (1.5 g, 5.8 mmol) in 45 mL of anhydrous THF at room temperature was added portionwise, sodium hydride (581 mg, 14.5 mmol). The mixture was stirred and heated to reflux for 2 hours and cooled to room temperature. 3,4-dichloro benzyl bromide (1.39 g, 5.8 mmol) was then added and the reaction mixture was heated to reflux for 1.5 hours, cooled to room temperature and stirred overnight. The reaction was quenched with ice-water (40 mL) and carefully acidified to pH 3 with 2N HCl. Extraction with ethyl acetate (100 mL) followed by a water (50 mL) and a brine (40 mL) wash gave, after drying ($Na_2SO_4$) and concentration in vacuo, a solid residue. Subjection of the crude mixture to flash chromatography (10% methanol-90% dichloromethane) provided 1.37 g (57%) of the desired product 2.

Synthesis of 5. Resin 4 (1.0 g, 0.65 mmol) (from Example 1) was placed in a Nalgene syringe equipped with a filter at the bottom and coupled to 2 (542 mg, 1.3 mmol) with HOBt (199 mg, 1.3 mmol), HBTU (493 mg, 1.3 mmol) and DIEA (679 mL, 3.9 mmol) in 8 mL of NMP (with shaking) for 72 hours. The solvent was removed by suction and the resin washed sequentially with NMP (3×8 mL) and dichloromethane (3×8 mL) to provide resin 5.

Synthesis of 6. The t-Boc protecting group was removed from the resin 5 (in the Nalgene syringe) with 25% (v/v) TFA/dichloromethane (10 mL) for 30 minutes (with shaking). The resin was washed with dichloromethane (3×7 mL), followed by 10% DIEA/dichloromethane (3×7 mL) and finally with dichloromethane (3×7 mL). To the resulting resin was added Fmoc-valine-N-carboxy anhydride (950 mg, 2.6 mmol) and 8 mL of NMP. The reaction mixture was agitated for 72 hours at room temperature and the solvent was removed by suction. The resin 6 was washed sequentially with NMP (3×7 mL) and dichloromethane (3×7 mL) and used directly for the next step.

Synthesis of 8. This compound was prepared from resin 6 (0.1 mmol) using an Applied Biosystems Model 433A Peptide synthesizer. $N^\alpha$-Fmoc-protected amino acid and pyrazine-2-carboxylic acid were added sequentially to resin 6 with standard coupling cycles using HBTU with HOBt as coupling agents in NMP to yield resin 8.

Syntheses of 107. The aldehyde was cleaved from the resin 8 by treatment with 10 mL of a solution of THF/30% formalin/AcOH/0.1N HCl 5:1:1:1 (v:v:v:v) for 1 hour at room temperature. After washing the resin with cleavage reagent (5 mL), the combined filtrates were diluted with water (15 mL) and 5 mL of that mixture was purified by RP-HPLC with a Waters DeltaPak 300 A C18 column (15 m, 30×300 mm) eluting with a linear acetonitrile gradient containing 0.1% TFA (v/v) over 45 minutes at 20 mL/minute. Fraction containing the desired product were pooled and lyophilized to provide 107. M+H=685.1.

EXAMPLE 8

Synthesis of Compound 108

Synthesis of 5. Resin 4 (640 mg, 0.414 mmol) (from Example 1) was placed in a Nalgene syringe equipped with a filter at the bottom and coupled to 1 (wherein X, Y and Z are hydrogen; 200 mg, 0.828 mmol) with HOBt (126 mg, 0.828 mmol), HBTU (314 mg, 0.828 mmol) and DIEA (433 mL, 3.9 mmol) in 6 mL of NMP (with shaking) for 24 h. The solvent was removed by suction and the resin washed sequentially with NMP (3×5 mL) and dichloromethane (3×5 mL) to provide resin 5.

Synthesis of 6. The t-Boc protecting group was removed from the resin 5 (in the Nalgene syringe) with 50% (v/v) TFA/dichloromethane (6 mL) for 20 minutes (with shaking). The resin was washed with dichloromethane (3×6 mL), followed by 10% DIEA/dichloromethane (3×6 mL) and finally with dichloromethane (3×6 mL). To the resulting resin was added Fmoc-valine-N-carboxy anhydride (605 mg, 1.66 mmol) and 10 mL of NMP. The reaction mixture was agitated for 72 hours at room temperature and the solvent was removed by suction. The resin 6 was washed sequentially with NMP (3×7 mL) and dichloromethane (3×7 mL) and used directly for the next step.

Synthesis of 8. This compound was prepared from resin 6 (0.1 mmol) using an Applied Biosystems Model 433A Peptide synthesizer. $N^\alpha$-Fmoc-protected amino acid and pyrazine-2-carboxylic acid were added sequentially to resin 6 with standard coupling cycles using HBTU with HOBt as coupling agents in NMP to yield resin 8.

Syntheses of 108. The aldehyde was cleaved from the resin 8 by treatment with 10 mL of a solution of THF/30% formalin/AcOH/0.1N HCl 5:1:1:1 (v:v:v:v) for 1 hour at room temperature. After washing the resin with cleavage reagent (5 mL), the combined filtrates were diluted with water (15 mL) and 5 mL of that mixture was purified by RP-HPLC with a Waters DeltaPak 300 A C18 column (15 m, 30×300 mm) eluting with a linear acetonitrile gradient containing 0.1% TFA (v/v) over 45 minutes at 20 mL/minute. Fraction containing the desired product were pooled and lyophilized to provide 108. M+H=511.3.

EXAMPLE 9

Synthesis of Compound 109

Synthesis of 5. Resin 4 (640 mg, 0.414 mmol) (from Example 1) was placed in a Nalgene syringe equipped with a filter at the bottom and coupled to 1 (238 mg, 0.828 mmol) with HOBt (126 mg, 0.828 mmol), HBTU (314 mg, 0.828 mmol) and DIEA (433 mL, 3.9 mmol) in 6 mL of NMP (with shaking) for 24 hours. The solvent was removed by suction and the resin washed sequentially with NMP (3×5 mL) and dichloromethane (3×5 mL) to provide resin 5.

Synthesis of 6. The t-Boc protecting group was removed from the resin 5 (in the Nalgene syringe) with 50% (v/v) TFA/dichloromethane (6 mL) for 20 minutes (with shaking). The resin was washed with dichloromethane (3×6 mL), followed by 10% DIEA/dichloromethane (3×6 mL) and finally with dichloromethane (3×6 mL). To the resulting resin was added Fmoc-valine-N-carboxy anhydride (605 mg, 1.66 mmol) and 10 mL of NMP. The reaction mixture was agitated for 72 hours at room temperature and the solvent was removed by suction. The resin 6 was washed sequentially with NMP (3×7 mL) and dichloromethane (3×7 mL) and used directly for the next step.

Synthesis of 8. This compound was prepared from resin 6 (0.1 mmol) using an Applied Biosystems Model 433A Peptide synthesizer. $N^\alpha$-Fmoc-protected amino acid and pyrazine-2-carboxylic acid were added sequentially to resin 6 with standard coupling cycles using HBTU with HOBt as coupling agents in NMP to yield resin 8.

Syntheses of 109. The aldehyde was cleaved from the resin 8 by treatment with 10 mL of a solution of THF/30% formalin/AcOH/0.1N HCl 5:1:1:1 (v:v:v:v) for 1 hour at room temperature. After washing the resin with cleavage reagent (5 mL), the combined filtrates were diluted with water (15 mL) and 5 mL of that mixture was purified by RP-HPLC with a Waters DeltaPak 300 A C18 column (15 m, 30×300 mm) eluting with a linear acetonitrile gradient containing 0.1% TFA (v/v) over 45 minutes at 20 mL/minute. Fraction containing the desired product were pooled and lyophilized to provide 109. M+H=561.3.

EXAMPLE 10

Synthesis of Para-Hydroxyanthranilic Acid Derivatives

The synthesis of compounds of the formulae:

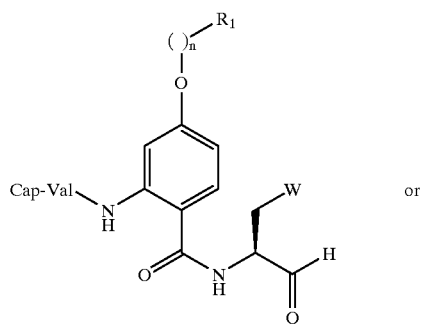

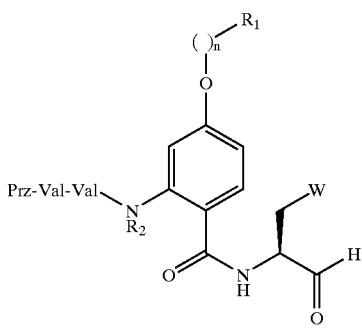

is achieved using the steps set forth in Scheme 1 to produce 9 or 10 and intermediate 1 containing a hydroxy group at Y and hydrogens at X and Z.

Synthesis of 1. This compound is prepared in three steps from 2-nitro-4-aminobenzoic acid. Diazotization of 2-Nitro-4-aminobenzoic with, for example, sodium nitrite in 20% sulfuric acid provides 2-nitro-4-hydroxybenzoic acid. Reduction of 2-nitro-4-hydroxybenzoic acid with, for example, tin in concentrated hydrochloric acid provide the desired p-hydroxyanthranilic acid. The amino group is then protected, for example, by treatment with, for example Boc anhydride in dichloromethane with diisopropylethylamine to give 1.

EXAMPLE 11

Scheme 2, set forth below, depicts the synthetic route to obtain alkyl-substituted anthranilic acid derivatives compounds of this invention.

SCHEME 2
General Syntheses for the Anthranilic Acids

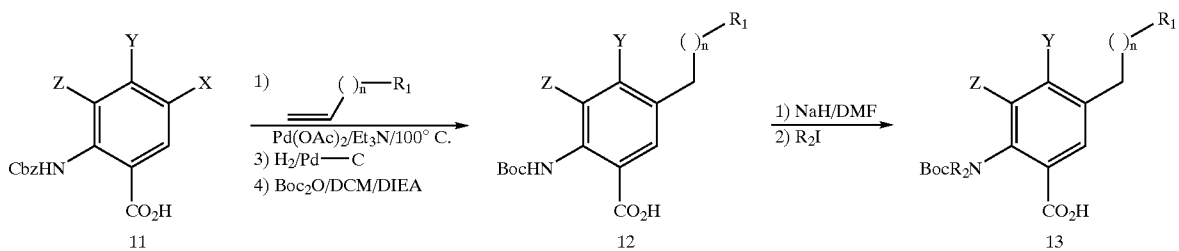

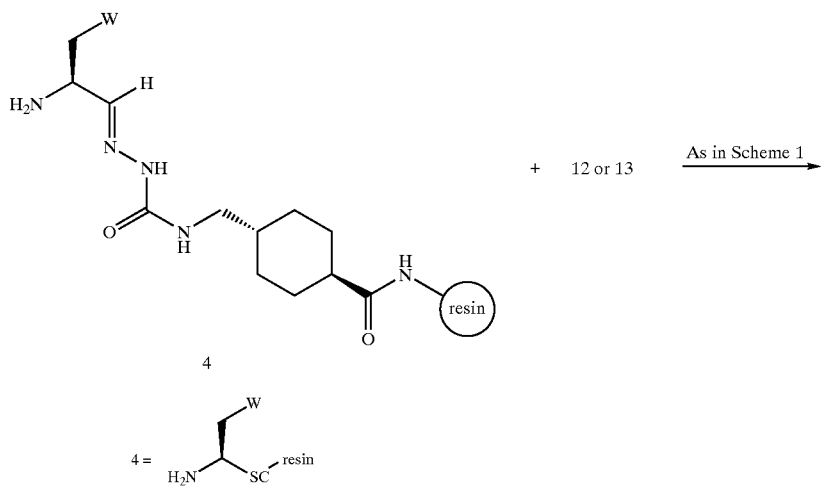

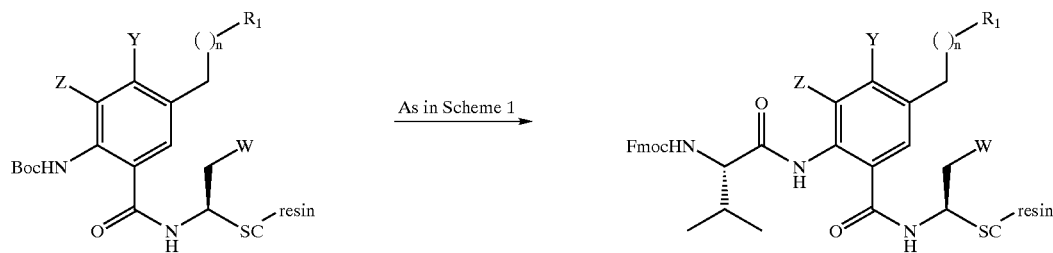

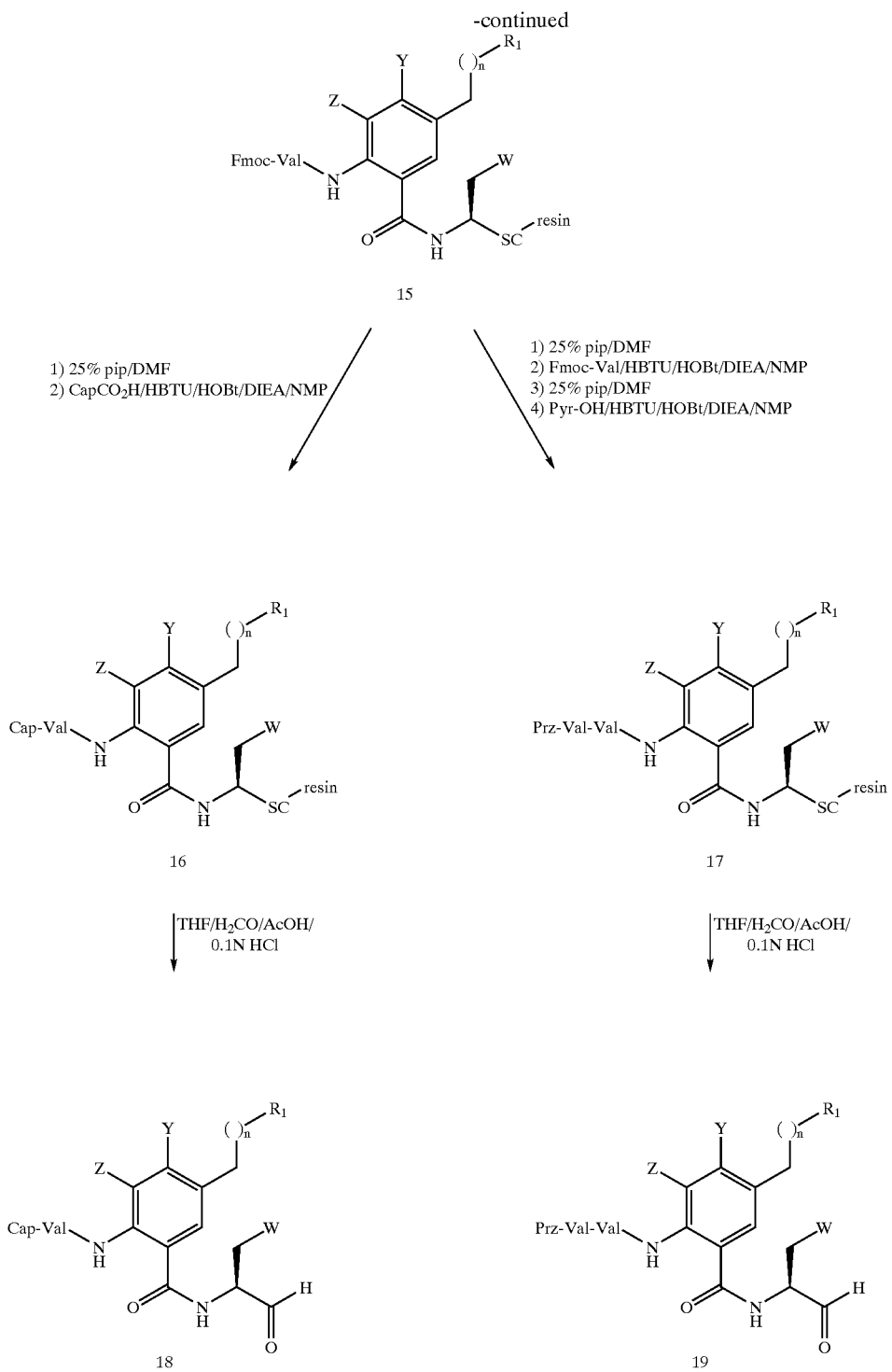

Synthesis of 12. This compound is prepared in three steps from the coupling of 11 (wherein X is Br; Y and Z are H) with styrene in a Heck reaction using palladium acetate and triethylamine. After deprotection and hydrogenation of the double bond with palladium on carbon followed by protection of the amino group as a carbamate with Boc anhydride in dichloromethane and DIEA compound 12 is obtained.

Para-alkyl-substituted anthranilic acid derivatives are similarly prepared using 11 wherein Y is Br and X and Z are H, similar to the method described in this example.

EXAMPLE 12

Carbazate-containing compounds of this invention (compounds 27 and 28) are produced according to Scheme 3, depicted below:

SCHEME 3.
General Syntheses for the Carbazates
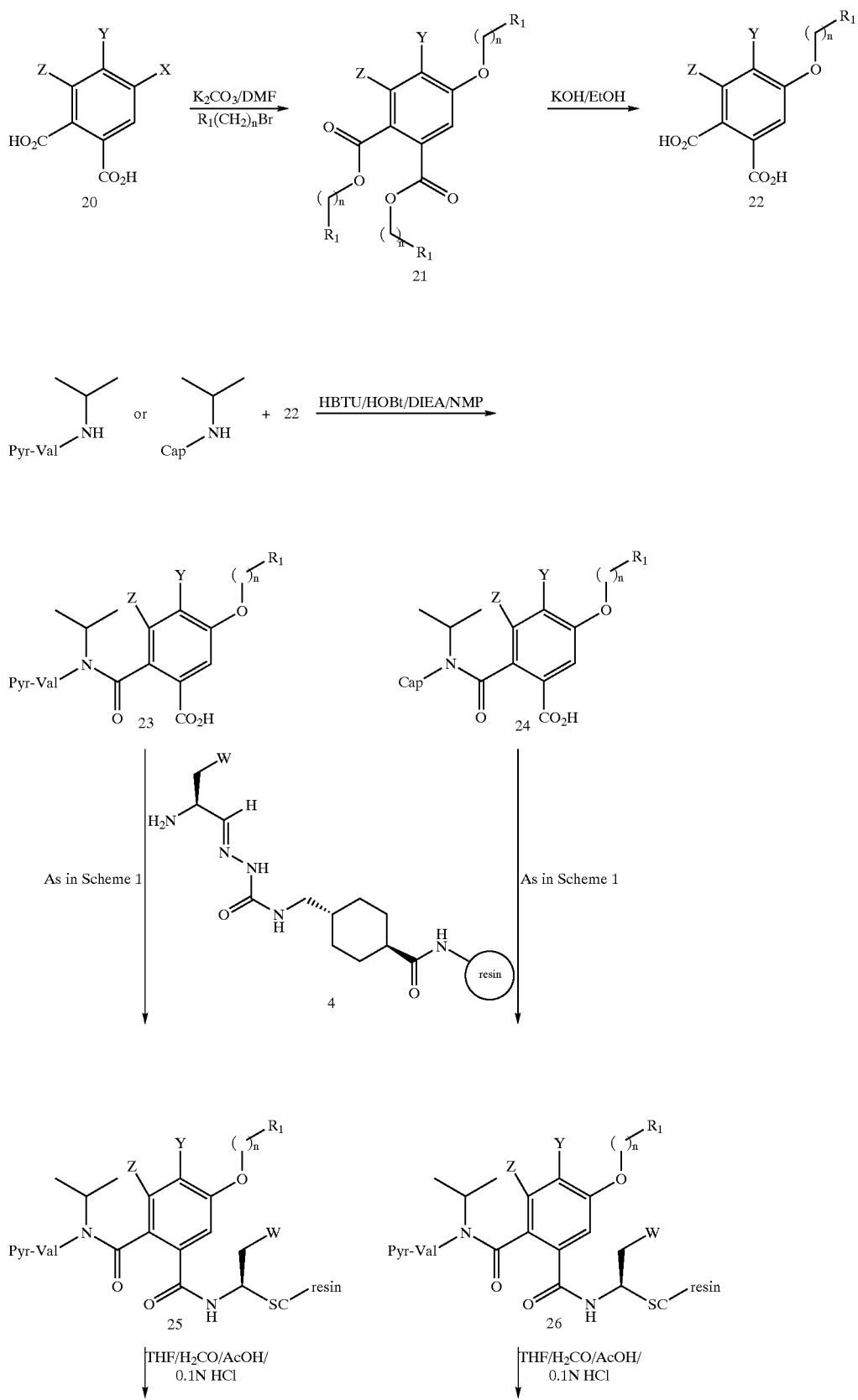

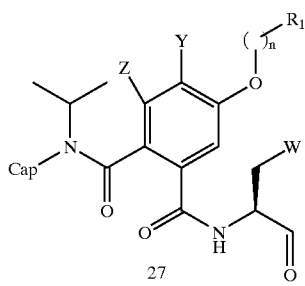

27

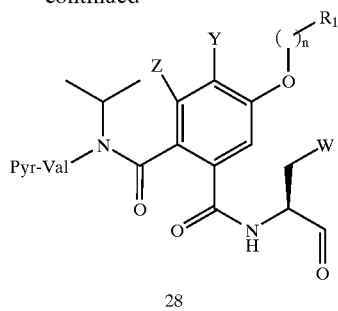

28

Synthesis of 22. This compound could be prepared for example, in two steps from 4-hydroxyphthaloic acid (20) by alkylation with, for example, an excess of benzyl bromide with a base such as potassium carbonate in dimethylformamide. After saponification of the diester 21 with, for example, potassium hydroxide in ethanol provide compound 22.

Synthesis of 23 and 24. These compounds could be prepared by coupling 22 with pyrazine-Val-isopropylcarbazate or with arylcarboxylic acid (Cap) isopropylcarbazate with, for example, HOBT, HBTU and DIEA in N-methylpyrrolidinone as previously described in Example 1 to provide 23 or 24.

Synthesis of 25 and 26. These resins could be prepared from resin 4 according to Scheme 3 and experimentals previously described in Example 1.

Syntheses of 27 and 28. These compounds could be prepared according to Scheme 2 and experimental previously described in Examples 1 and 2.

EXAMPLE 13

1,4-diketone-containing compounds of this invention (compounds 32 and 33) are produced according to Scheme 4, depicted below:

SCHEME 4.
General Syntheses for the 1,4-Diketones

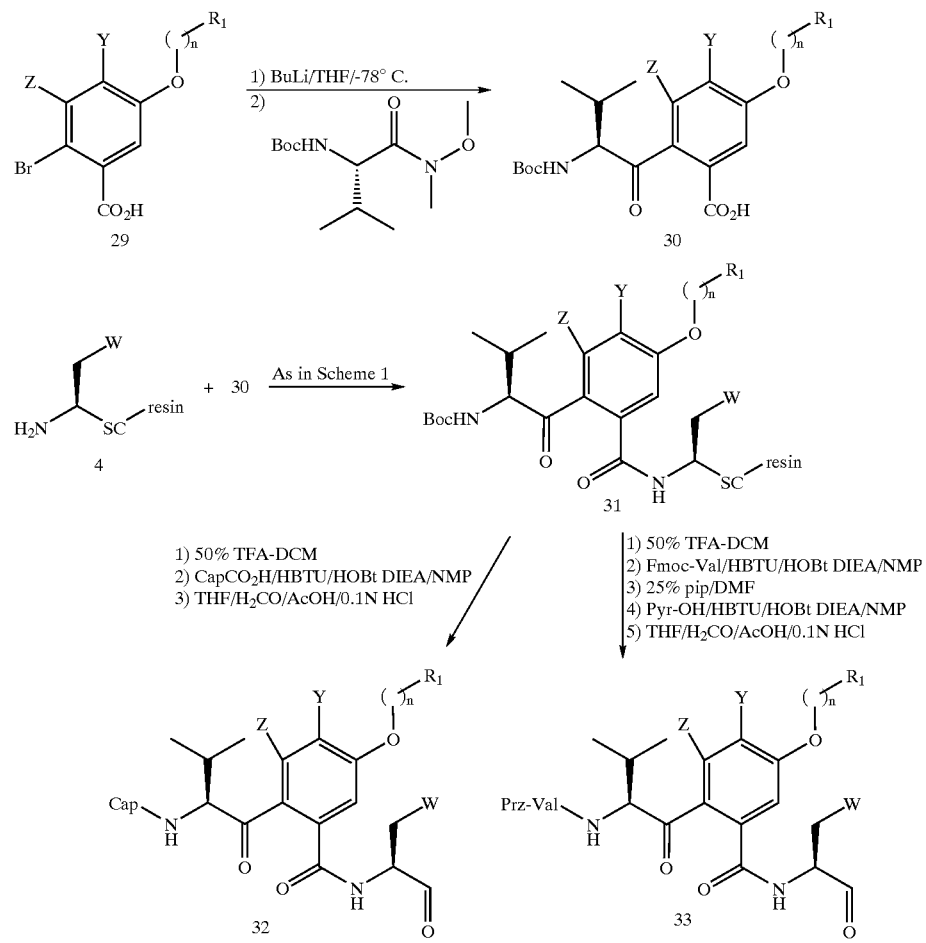

Synthesis of 30. This compound is prepared from 29 by deprotonation/halogen-metal exchange with a base, such as butyl lithium in tetrahydrofuran, followed by addition of Boc-Val-C(O)N(OMe)Me (Weinreb amide).

Syntheses of 32 and 33. These compounds are prepared according to Scheme 4 and experimentals previously described in Examples 1 and 2.

EXAMPLE 14

1,2-diketone-containing compounds of this invention (compounds 39 and 40) are produced according to Scheme 5, depicted below:

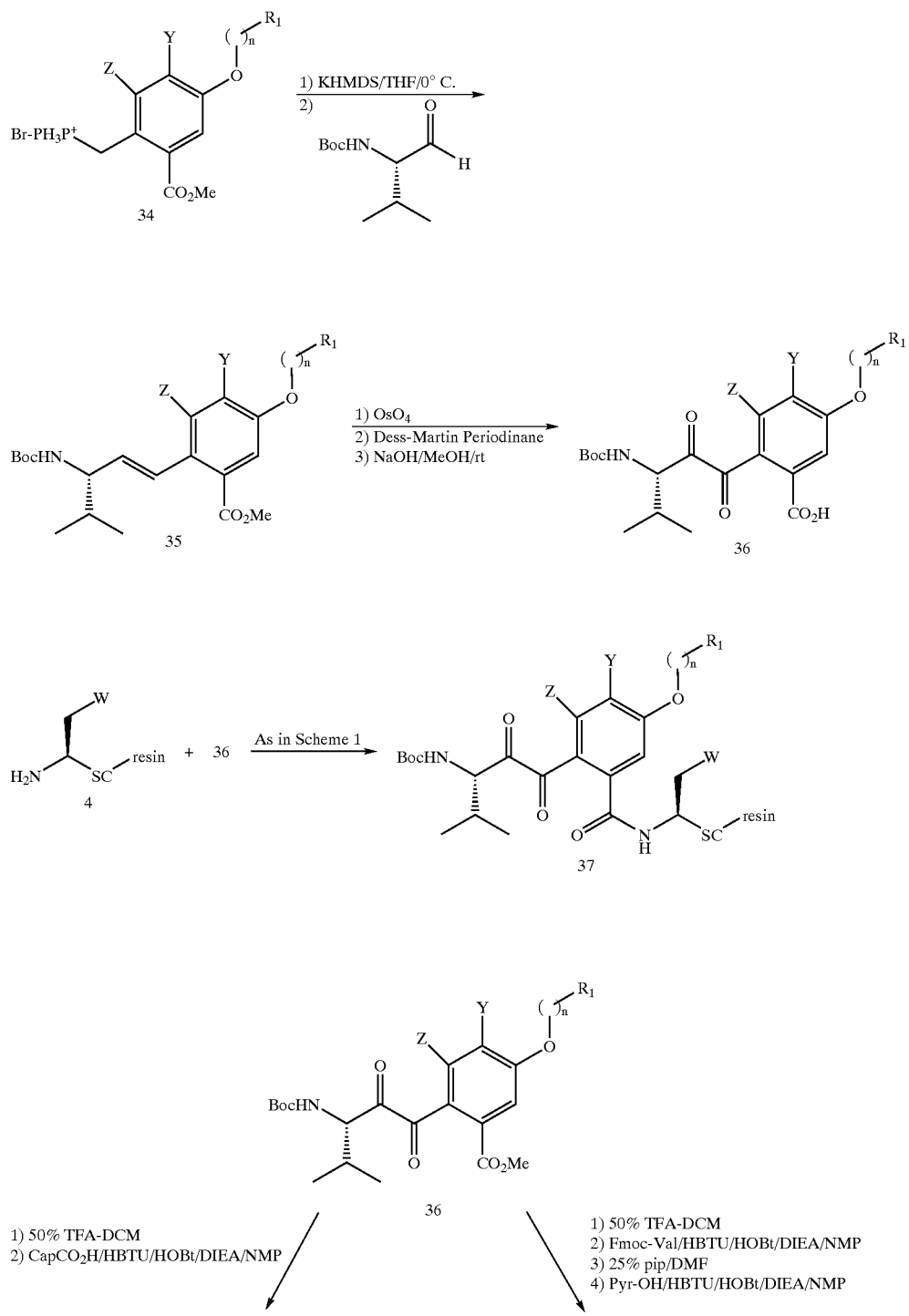

SCHEME 5.
General Syntheses for the 1,2-Diketones

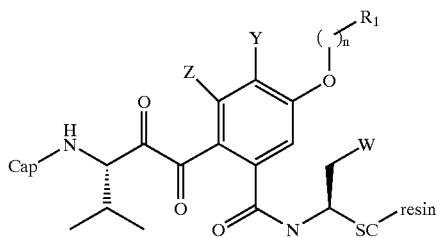

37

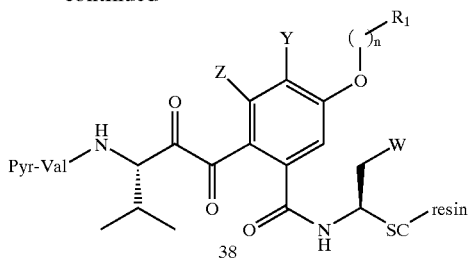

38

THF/H₂CO/AcOH/
0.1N HCl

THF/H₂CO/AcOH/
0.1N HCl

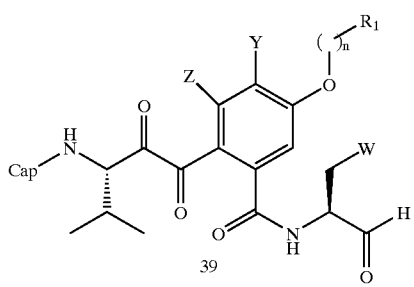

39

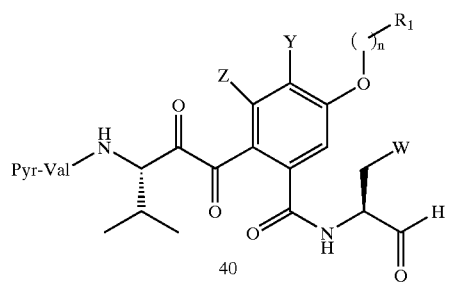

40

Synthesis of 35. This compound is prepared from phosphonium bromide 34 by treatment with a base such as potassiumn hexamethyldisilazide in tetrahydrofuran, followed by addition of Boc-Val-H. Synthesis of 36. This compound is prepared from olefin 35 by an osmylation reaction with, for example, osmium tetraoxide and oxidation of the resulting diol with, for example, Dess-Martin periodinane. This step is followed by a saponification reaction with, for example, sodium hydroxide in methanol.

Syntheses of 39 and 40. These compounds are prepared according to Scheme 5 and experimentals previously described in Examples 1 and 2.

EXAMPLE 15

Sulfone-containing compounds of this invention (compounds 47 and 48) are prepared according to Scheme 6, below:

SCHEME 6.
General Syntheses for the Sulfonamides

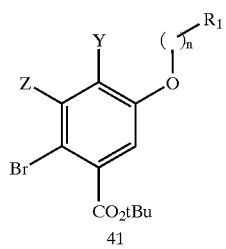

41

1) Mg/ether
2) SO₂

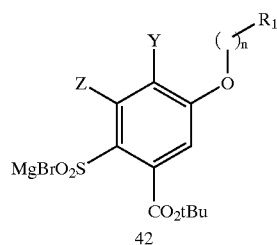

42

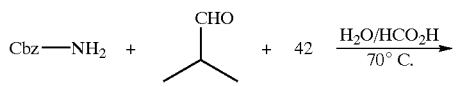

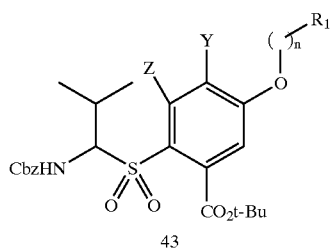

43

1) H₂/Pd—C
2) 5% TFA
3) Fmoc-OSU
   dioxane/H₂O

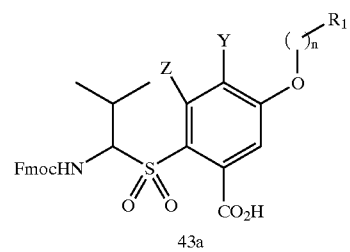

43a

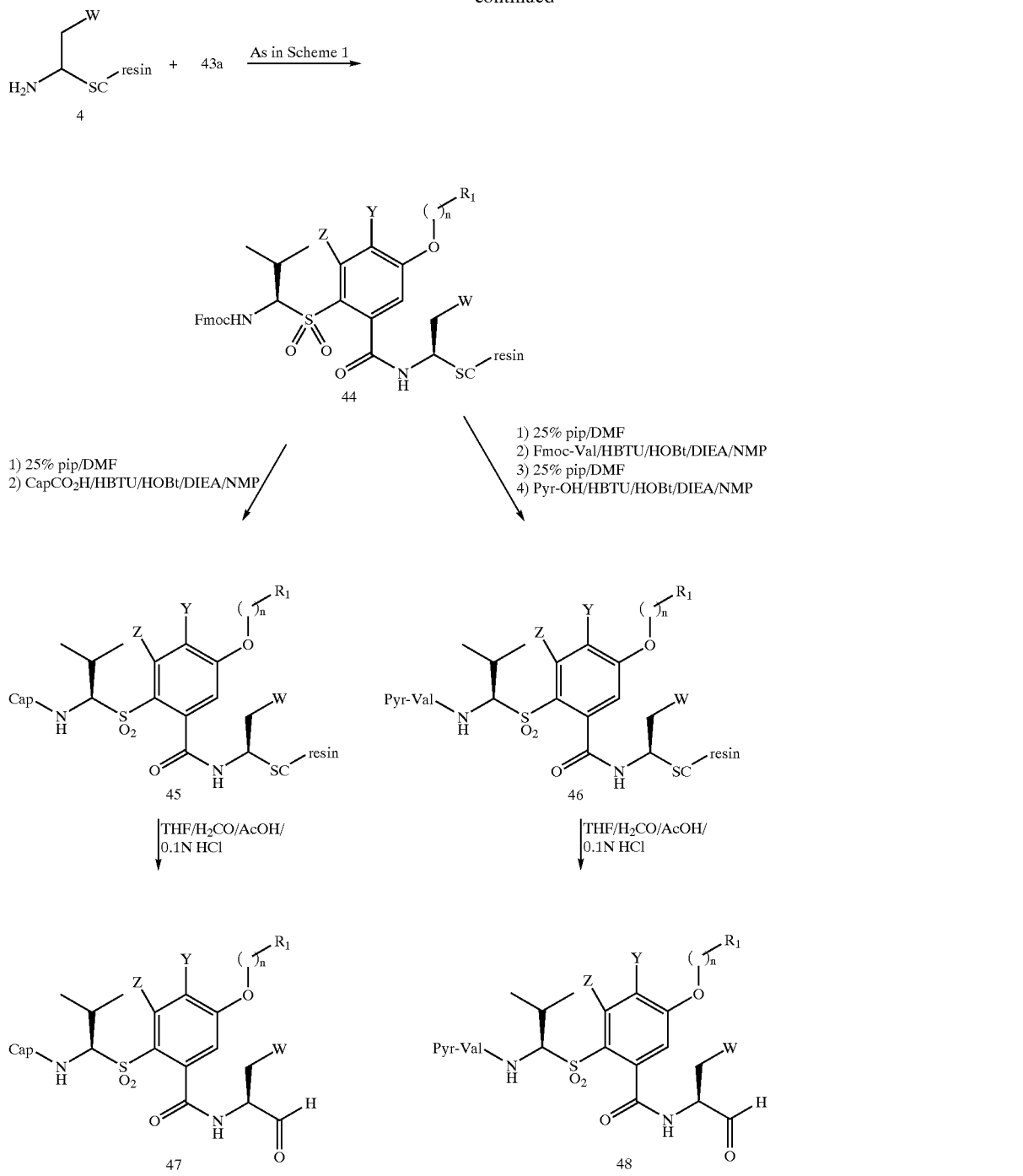

Synthesis of 42. This compound is prepared from bromoester 41 by treatment with magnesium in ether followed by addition of sulfur dioxide to the mixture.

Synthesis of 43. This compound is prepared from a mixture of sulfinate salt 42 and benzylcarbamate in water by treatment with isobutyraldehyde in methanol. This step is followed by addition of formic acid with heating.

Synthesis of 43a. This compound is prepared by deprotection of the amino group of compound 43 with hydrogen over palladium on carbon. This is followed by saponification of the ester with 5% TFA in dichloromethane, followed by treatment with Fmoc-OSU in dioxane-water.

Syntheses of 47 and 48. These compounds are prepared according to Scheme 6 and experimentals previously described in Examples 1 and 2.

EXAMPLE 16

Sulfonyl-carbazate-containing compound of this invention (compounds 54 and 55) are prepared according to Scheme 7, depicted below.

SCHEME 7.
General Syntheses for the Sulfonyl Carbazates
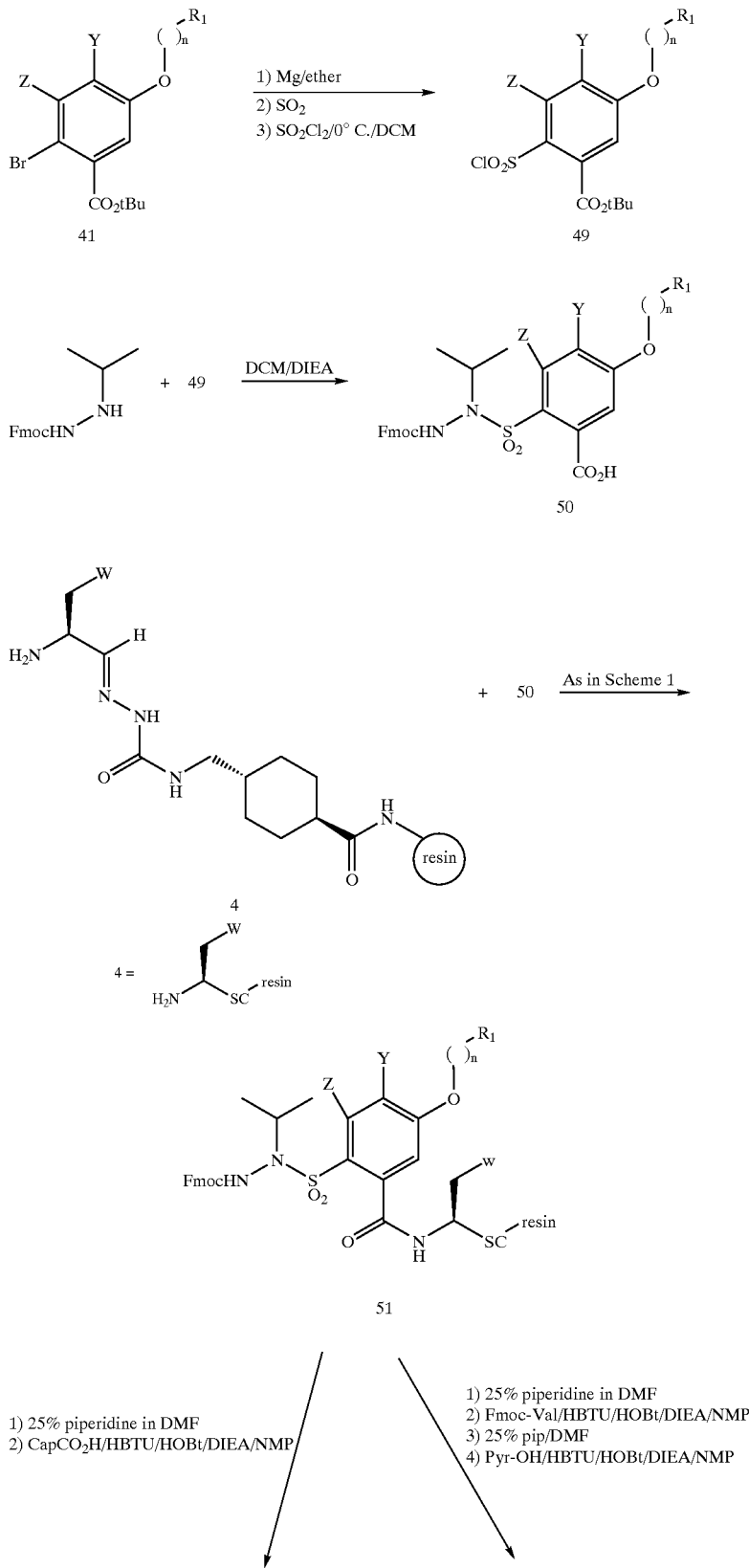

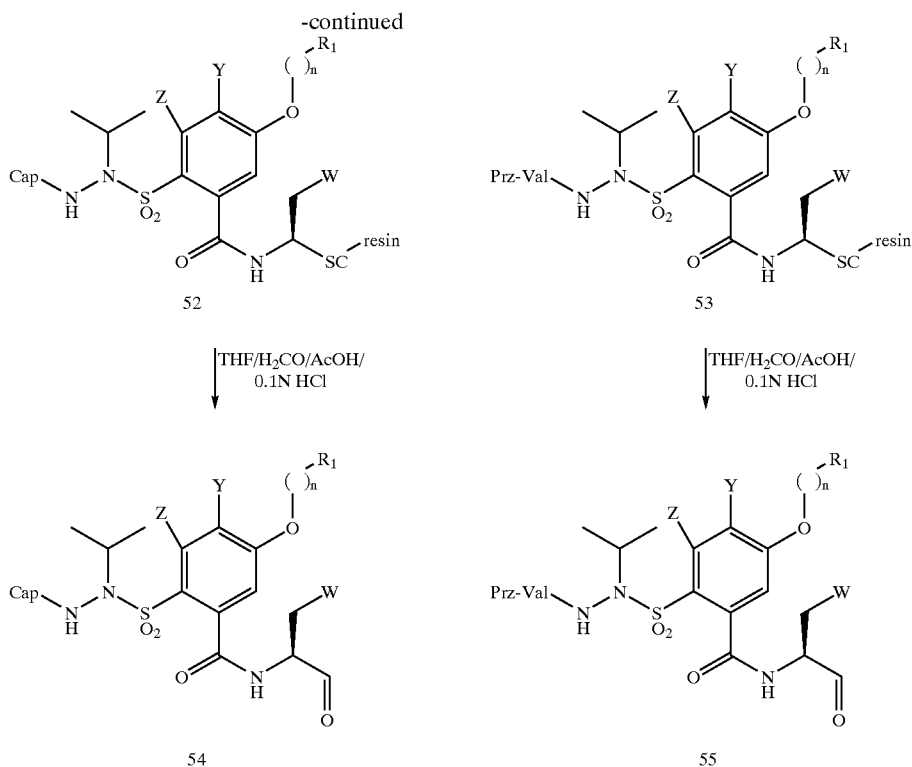

Synthesis of 49. This compound is prepared from bromoester 41 by treatment with magnesium in ether, followed by addition of sulfur dioxide to the mixture and subsequent treatment with sulfuryl chloride in dichloromethane at 0° C.

Synthesis of 50. This compound is prepared by coupling sulfinate 49 and Fmoc-isopropylcarbazate in the presence of DIEA in dichloromethane, followed by treatment with 5% TFA in dichloromethane.

Syntheses of 54 and 55. These compounds are prepared according to Scheme 7 and experimentals previously described in Examples 1 and 2.

EXAMPLE 17

Sulfonamide-containing compounds of this invention (compounds 62 and 63) are prepared according to Scheme 8, depicted below.

SCHEME 8.
General Syntheses for the Sulfonamides

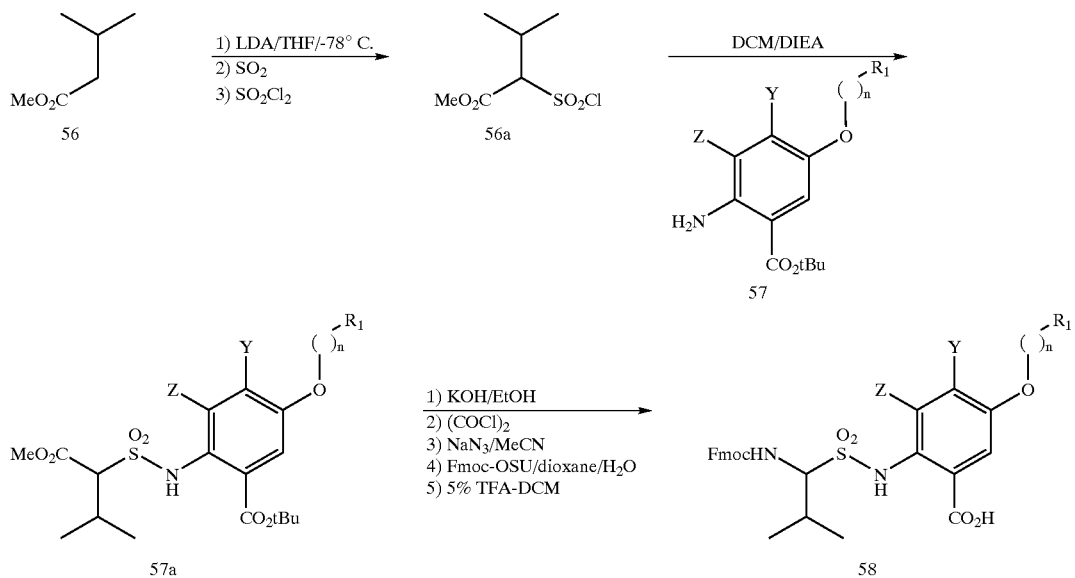

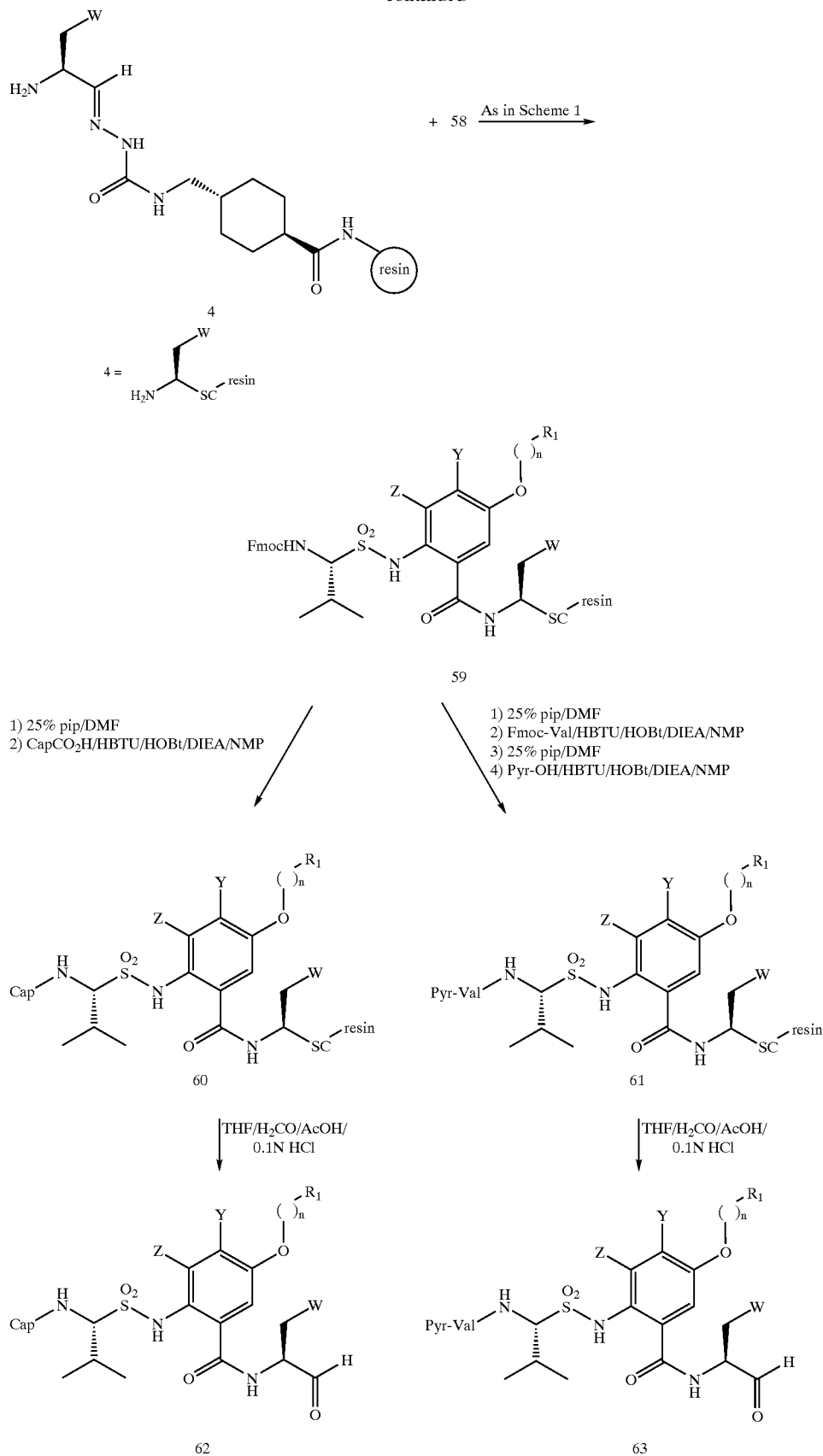

Synthesis of 56a. This compound is prepared from ester 56 by treatment with lithium diisopropylamide in THF at −78° C. followed by addition of sulfur dioxide to the mixture and subsequent treatment with sulfuryl chloride in dichloromethane at 0° C.

Synthesis of 57a. This compound is prepared by coupling sulfonyl chloride 56a and anthranilate 57 in the presence of DIEA in dichloromethane.

Synthesis of 58. This compound is prepared by saponification of 57a with potassium hydroxide in ethanol followed by a Curtius rearrangement using, for example, oxalyl chloride with sodium azide in acetonitrile. Protection of the amino functional group with Fmoc-OSU in dioxane-water, followed by hydrolysis of the t-butyl ester with 5% TFA in dichloromethane provide compound 58.

Syntheses of 62 and 63. These compounds could be prepared according to Scheme 8 and experimentals previously described in Examples 1 and 2.

It will be readily apparent to those of skill in the art that other compounds of this invention may be synthesized using variations of Schemes 1 through 8 and/or the appropriate variants of the reagents depicted in those schemes and set forth in Examples 1 through 17.

EXAMPLE 18

Inhibition of HCV NS3 Serine Protease

Insofar as compounds of formula (I) are able to inhibit NS3 serine protease, they are of evident clinical utility for the treatment of viral diseases, including HCV. These tests are predictive of the compounds ability to inhibit HCV in vivo.

Peptides and Assays.

Peptides EDVVabuCSMSY (Abu designates—aminobutyric acid), DEMEECSQHLPYI, ECTTPCSG-SWLRD and EDVV AbuC-p-nitroanilide was purchased from AnaSpec Inc. (San Jose, Calif.).

Peptide content of purified, lyophilized peptides and in-house peptides was determined by quantitative nitrogen analysis and the appropriate values were used in preparing stock peptide solutions (Galbreath). pKa determinations were determined by Robertson Microlit Laboratories, Inc. (Madison, N.J.).

HPLC cleavage assays were performed using 25 nM to 3.0 µM enzyme in 100 µL volumes at 30 C containing 50 mM HEPES-KOH (pH 7.8), 100 mM NaCl, 20% glycerol, 5 mM DTT and the appropriate amount of substrate (in DMSO), with or without NS4A peptide, such that the final concentration of DMSO did not exceed 4%. Separate control experiments verified that this percentage of DMSO did not effect enzymatic activity. Cleavage reactions were quenched by the addition of an equal volume of a mixture of 10% TFA: acetonitrile (1:1) and activity was assessed on a reversed phase HPLC column (Rainin C18 Microsorb-MV, 5mm, 4.6×250mm; 0–50% acetonitrile, 0.1% TFA @ 3.33% min) using a Hewlett Packard 1050 instrument with auto-injection and diode array detection at 210 nm and 280 nm (where appropriate). Peptide elution fragments were collected and identified by mass spectrometry and N-terminal sequence analysis. Fragment identity and concentration was further verified by authentic, synthesized products. Initial rates of cleavage were determined at <20% substrate conversion and catalytic parameters were determined assuming Michaelis-Menten kinetics using the MultiFit program (Day Computing, Cambridge, Mass.).

Spectrophotometric assays were run in a 96-well microtiter plate at 30 C, using a SpectraMax 250 reader (Molecular Devices, Sunnyvale, Calif.) with kinetic capability. Cleavage of EDVV AbuC-p-nitroanilide (5A-pNA) substrate was performed with or without NS4A in the same buffer used for HPLC assays at 30 C, and pNA release was monitored at 405 nm. The extinction coefficient of p-nitroaniline is independent of pH at values of 5.5. and above [Tuppy, H., et al., *Hoppe-Seyler's Z. Physiol. Chem.*, 329, pp. 278–288 (1962)]; Raybuck and Luong, unpublished observations). The percentage of DMSO did not exceed 4% in these assays.

Determination of the pH dependence of Vmax, $K_m$ and $V_{max}/K_m$ was performed using a series of constant ionic strength buffers containing 50 mM MES, 25 nM Tris, 25 mM ethanolamine and 0.1 M NaCl [Morrison, J. F. and Stone, R. F., *Biochemistry*, 27, pp. 5499–5506 (1988)]. The inflection point for log V data was calculated by nonlinear least squares fit of the data to the equation.

$$\log v = \log[V\mathrm{max}/(1+H/K_a)]$$

[Dixon, M. and Webb, E. C. Enzymes; Academic Press: New York; Vol., pp. 138–164 (1979)]. The inflection points for log (V/K) data were calculated by nonlinear least squares fit of the data to the equation:

$$\log v = \log[V\mathrm{max}/(1+H/K_a+K_b/H)]$$

[Dixon, M. and Webb, E. C. Enzymes; Academic Press: New York; Vol., pp. 138–164 (1979)]. The program KineTic (BioKin Ltd) was used in both cases.

Kinetic constants for the rapid equilibrium ordered bisubstrate reaction were determined from rate vs. [4A], [EDVV AbuC-pNA] data by non-linear least squares fitting to equation 1 [Morrison, J. F. *Biochim. Biophys. Acta.*, 185, pp. 269–286 (1969)] as described in the text. $K_{ii}$ and $K_{is}$ values for peptidyl inhibitors were determined from rate vs. [inhibitor], [substrate] data and fitting to the equation for mixed inhibition:

$$\mathrm{rate} = V\mathrm{max}[S]/\{K_m(1+[I]/K\mathrm{is})+[S](1+[I]/K\mathrm{ii})\}$$

The commercial program KinetAsyst (State College, Pa.) was used for both procedures. Ki values were calculated from rate vs. [inhibitor] plots by a nonlinear least squares fit of the data to the equation of Morrison for tight binding competitive inhibition [Morrison, J. F. *Biochim. Biophys. Acta.*, 185, pp. 269–286 (1969)]. The KineTic program (BioKin Ltd) was used for this procedure.

The results are shown in Table 2. $K_i$ values are expressed in µM. Category "A" indicates <1 µM inhibition; category "B" indicates 1–100 µM inhibition; category "C" indicates >100 µM. The designation "ND" indicates that the compound was not tested.

TABLE 2

Enzyme inhibition data for compounds 1–9.

| Compound | $K_1$ |
|---|---|
| 101 | B |
| 102 | B |
| 103 | B |
| 104 | B |
| 105 | B |
| 106 | B |
| 107 | B |
| 108 | ND |
| 109 | ND |

While we have hereinbefore presented a number of embodiments of this invention, it is apparent that my basic construction can be altered to provide other embodiments which utilize the methods of this invention. Therefore, it will be appreciated that the scope of this invention is to be defined by the claims appended hereto rather than the specific embodiments which have been presented hereinbefore by way of example.

What is claimed is:

1. A compound of the formula (I):

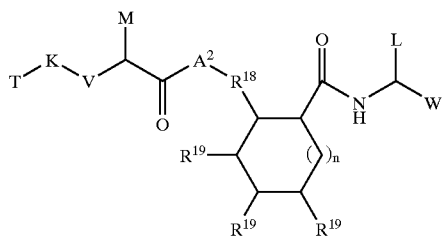

wherein:

W is:

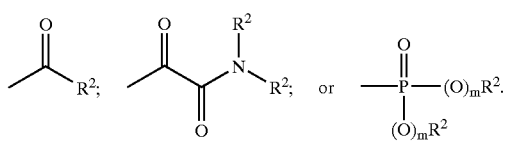

wherein:
m is 0 or 1;
each $R^2$ is H;
J is selected from t-butyl, methyl, trifluoromethyl, hydroxy, methoxy, ethoxy, trifluoromethoxy, carboxy, phenyl, benzyl, phenoxy, benzyloxy, fluoro, chloro, bromo, isoxazolyl, pyridinyl, piperidinyl, carboxymethyl, carboxyethyl, dialkylamino, morpholinylmethyl, phenylacetylamino, or acylamino, wherein each J is optionally substituted with 1–3 $J^1$ groups;
each $J^1$ is independently selected from $C_{1-3}$ alkoxy, chloro, $C_{1-3}$ alkyl, or phenyl;
L is $CH_2CH_3$ or $CH_2CF_3$;
each M is independently selected from isopropyl, propyl, methyl, pyridylmethyl, benzyl, naphthylmethyl, phenyl, imidazolylmethyl, thiophenylmethyl, cyclohexylmethyl, phenethyl, benzylthiomethyl, or benzyloxyethyl;
$R^{18}$ is —N($R^{11}$)—;
$R^{11}$ is hydrogen or $C_1$–$C_3$ alkyl;
one $R^{19}$ is —O—($C_1$–$C_3$)-alkyl-aryl and the other two $R^{19}$ are H; or two adjacent $R^{19}$ are bound together to form phenyl ring and the other $R^{19}$ is H;
n is 1;
the ring to which $R^{18}$ and $R^{19}$ are attached is phenyl;
$A^2$ is a bond or —N($R^{11}$)—C(H)(M)—C(O)—;
V is —N($R^{11}$)—;
K is —C(O)—; and
T is —$R^{12}$ or -alkyl-$R^{12}$;
wherein:
each $R^{12}$ is independently aryl or heteroaryl and is optionally substituted with 1 to 3 J groups.

2. The compound according to claim 1, wherein W is —C(O)H.

3. The compound according to claim 1, wherein each M is isopropyl.

4. The compound according to claim 1, wherein one $R^{19}$ is —O-benzyl.

5. The compound according to claim 1, wherein $R^{18}$ is —N(H)— or —N(CH$_3$)—.

6. The compound according to claim 1, wherein $A^2$ is a bond or —N(H)—C(H)(M)—C(O)—, wherein M is isopropyl.

7. The compound according to claim 1, wherein V is —NH—.

8. The compound according to claim 1, wherein $R^{12}$ is naphthyl, pyrazinyl, or pyridyl, any of which is optionally substituted with a hydroxy group.

9. A pharmaceutically acceptable composition comprising:
a) compound according to any one of claims 1, 2, 3, 4, 5, 6, 7, or 8 in an amount effective to inhibit HCV NS3 protease; and
b) a pharmaceutically suitable carrier.

10. A method for inhibiting serine protease activity in a patient comprising the step of administering to said patient a pharmaceutical composition according to claim 9 in an amount effective to inhibit serine protease activity.

11. The method according to claim 10, wherein the serine protease is HCV NS3 protease.

12. A method for treating a hepatitis C viral infection in a patient comprising the step of administering to said patient a pharmaceutical composition according to claim 9.

13. A process for preparing a compound of formula (I) according to claim 1, comprising the step of reacting a compound of formula (II):

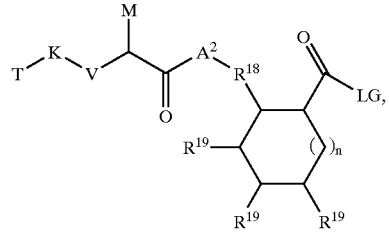

wherein LG is —OH or an appropriate leaving group, and the other substituents are as defined in claim 1;

with a compound of formula (III):

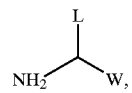

wherein the NH$_2$ group is optionally protected, and L and W are as defined in claim 1;

in the presence of a coupling agent, provided that the compound of formula (II) or the compound of formula (III) is optionally bound to a resin.

* * * * *